(12) United States Patent
Debart et al.

(10) Patent No.: US 8,536,318 B2
(45) Date of Patent: Sep. 17, 2013

(54) CHEMICAL RNA SYNTHESIS METHOD

(75) Inventors: Françoise Debart, Combaillaux (FR); Jean-Jacques Vasseur, Combaillaux (FR); Thomas Lavergne, Saint Clement de Riviere (FR)

(73) Assignees: Centre National de la Recherche Scientifique, Paris (FR); Universite Montpellier 2, Montpellier (FR)

( * ) Notice: Subject to any disclaimer, the term of this patent is extended or adjusted under 35 U.S.C. 154(b) by 136 days.

(21) Appl. No.: 12/995,001

(22) PCT Filed: May 28, 2009

(86) PCT No.: PCT/FR2009/000624
§ 371 (c)(1), (2), (4) Date: Feb. 22, 2011

(87) PCT Pub. No.: WO2009/144418
PCT Pub. Date: Dec. 3, 2009

(65) Prior Publication Data
US 2011/0275793 A1    Nov. 10, 2011

(30) Foreign Application Priority Data
May 29, 2008   (FR) ..................... 08 02928

(51) Int. Cl.
*C07H 21/02*   (2006.01)

(52) U.S. Cl.
USPC ........................................ 536/23.1

(58) Field of Classification Search
USPC ........................................ 536/23.1
See application file for complete search history.

(56) References Cited

U.S. PATENT DOCUMENTS 4,458,066 A * 7/1984 Caruthers et al. .......... 536/25.34
8,304,532 B2 * 11/2012 Adamo et al. ............. 536/25.34

FOREIGN PATENT DOCUMENTS

CN           1900103 A     1/2007

OTHER PUBLICATIONS

International Search Report from corresponding International Appl. No. PCT/FR2009/000624, mailed Nov. 13, 2009.
Written Opinion from corresponding International Appl. No. PCT/FR2009/000624, mailed Nov. 13, 2009.
Hoffman et al., "Synthesis of the Trioxadecalin-Part of Mycalamide B," *Tetrahedron Letters*, vol. 34, No. 49, 1993, pp. 7903-7906.
Parey et al., "First Evaluation of Acyloxymethyl or Acylthiomethyl Group as Biolabile 2'-O-Protections of RNA," *Organic Letters*, vol. 8, No. 17, 2006, pp. 3869-3872.

* cited by examiner

*Primary Examiner* — Jon E Angell
(74) *Attorney, Agent, or Firm* — Alston & Bird LLP

(57) ABSTRACT

The invention relates to a method for the chemical synthesis of RNA, comprising the following steps: a) bonding to a solid support of a monomer having formula (II) in which—$X_1$ is a dimethoxytrityl group,—$X_6$ is H or an OAc group or $OX_3$, in which $X_3$ is a group having formula (A), in which X is O or S, R' is H or $CH_3$ and R is selected from a linear or branched alkyl group at $C_1$ to $C_4$ and a $R_1$—O—$R_2$ group in which $R_1$ is an alkyl group at $C_1$ to $C_2$ and $R_2$ is a $CH_3$ group or $CH_2CH_2$—O—$CH_3$ or aryl; b) assembly with the monomer having formula (II) bound to the support thereof obtained in step (a) of at least one monomer having formula (III) in which $X_1$, Bp, $X_3$ are as defined for formula (II) and $X_5$ is a hydrogen phosphonate monoester or phosphoramidite group, preferably a 2-cyanoethyl-N,N-diisopropylphosphoramidite group, which is used to obtain a protected single-strand RNA bound to a support.

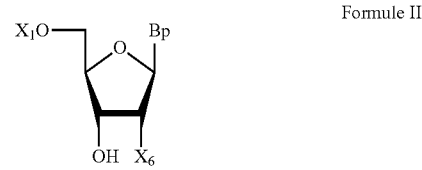

Formule II

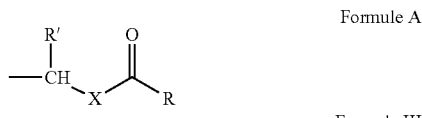

Formule A

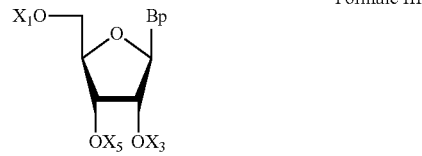

Formule III

5 Claims, No Drawings

CHEMICAL RNA SYNTHESIS METHOD

FIELD OF THE INVENTION

The invention relates to a method of RNA synthesis, a method of releasing a protected RNA and a method of synthesis of protected ribonucleotide monomers.

BACKGROUND OF THE INVENTION

Since the discovery of RNA interference (RNAi), a crucial need has arisen for small synthetic RNAs, in particular small oligoribonucleotides with a length of 21 nucleotides (siRNA), for biological research and therapeutic applications.

The ribonucleotide units constituting these RNAs can be natural ribonucleotide units or ones that have been modified, whether by modification of the nucleic acid base or of the ribose ring, as known in the prior art, and in particular as described in Watts, J. K. et al., Drug Discovery Today, Vol. 13, 19/20, October 2008, Schram K. H. et al., Mass Spectrometry Reviews, 1998, 17, 131-251, and Porcher et al., Helvetica Chimica Acta, Vol. 88, 2005, pages 2683-2704.

Compared with the synthesis of DNA, the production of synthetic RNAs is more complex owing to the presence of the hydroxyl function in position 2' of the ribose sugar that has to be protected. Finding the ideal protecting group is a crucial point for successful RNA synthesis. In addition to the lower coupling yields in assembly of the chain in comparison with the synthesis of DNA, the main difficulty in RNA chemistry arises from the instability of RNA in a basic medium.

That is why it is generally assumed in this field that the standard synthesis strategy used for the production of oligodeoxyribonucleotides (small DNAs), where all the reactive functions of the DNA are protected with protecting groups that are base-labile, i.e. are removed at the end of the process of chemical elongation by a single treatment with a base, is not applicable to the production of oligoribonucleotides (small RNAs).

Just as for the synthesis of DNA, the two routes most commonly used at present for synthesizing RNAs by the chemical route are, on the one hand, the route with phosphoroamidites, and on the other hand, the route with hydrogen phosphonates (H-phosphonates).

In the route with phosphoroamidites, monomers functionalized at 3' by a phosphoroamidite group are assembled, the assembled RNA then having a 3'-5' internucleotide phosphate linker protected, preferably, by a cyanoethyl group.

The trimethylsilylethyl (TSE) group can also be used as the protecting group for phosphates, as taught for example in Parey et al. "First Evaluation of Acyloxymethyl or Acylthiomethyl Groups as Biolabile 2'-O-Protections of RNA", Organic Letters, 2006, Vol. 8, No. 17, 3869-3872. However, it is stated in this document that the TSE group was selected because, in contrast to the cyanoethyl group, it is not removed in basic conditions but by fluoride ions. It is also stated in this document that in reality the TSE group was removed by the iodine solution used for the oxidation carried out for obtaining the 3'-5' phosphodiester linkers.

In the route with hydrogen phosphonates, monomers functionalized at 3' by a hydrogen phosphonate monoester group are assembled, the assembled RNA then having a 3'-5' internucleotide linker, which is a hydrogen phosphonate diester linker, which is then oxidized to phosphate. In this route, the RNA obtained at the end of elongation and after oxidation has unprotected 3'-5' phosphate internucleoside linkers.

In the route with phosphoroamidites, it is generally assumed in the art that protection of the hydroxyl in position 2' of the ribose sugar must not be effected with a base-labile protecting group that would be removed at the same time as the protecting group of the phosphate, which would lead to nucleophilic attack by the hydroxyl in position 2' of the phosphorus atom in the internucleotide linkers resulting in 2'-5' isomerization of the natural 3'-5' linkers or in rupture of the 3'-5' linker in the conditions of basic deprotection.

Thus, T. KEMPE et al., in "Nucleic Acids Research", 1982, 10, 6695-6714, reported very low yields in synthesis of oligoribonucleotides by protecting the hydroxyl group in position 2' of the ribose, with an acyl group such as an acetyl or benzoyl group.

The tert-butyldimethylsilyl (TBDMS) group is certainly the most used for protecting the hydroxyl at 2' of the ribose. Although several protecting groups have been proposed for replacing it, such as the triisopropylsilyloxymethyl (TOM), bis(2-acetoxyethyloxy)methyl (ACE), tert-butyldithiomethyl (DTM), 1-(2-cyanoethoxy)ethyl (CEE), 2-cyanoethoxymethyl (CEM), 2-(4-toluylsulfonyl)ethoxymethyl (TEM), levulinyl and 2-cyanoethyl groups, most of these groups are, like TBDMS, removed by fluoride ions. However, deprotection by fluoride ions is a major obstacle for obtaining pure oligoribonucleotides because of their contamination with salts, leading to long additional procedures for purification.

SUMMARY OF THE INVENTION

The invention aims to overcome the drawbacks of the methods of chemical RNA synthesis of the prior art, both of siRNA and of RNA of greater length, both of RNA comprising natural nucleic acid bases and modified nucleic acid bases or RNA comprising a natural or modified ribose ring, by proposing a method of RNA synthesis that uses a protecting group of the hydroxyls in position 2' of the ribose that can be removed by a base, without nucleophilic attack of the phosphorus atom and without rupture of the 3'-5' linkers of the RNA.

For this purpose, the invention proposes a method of releasing a single-stranded RNA, from a single-stranded RNA that is protected and attached by a linker to a solid substrate, of the following formula I:

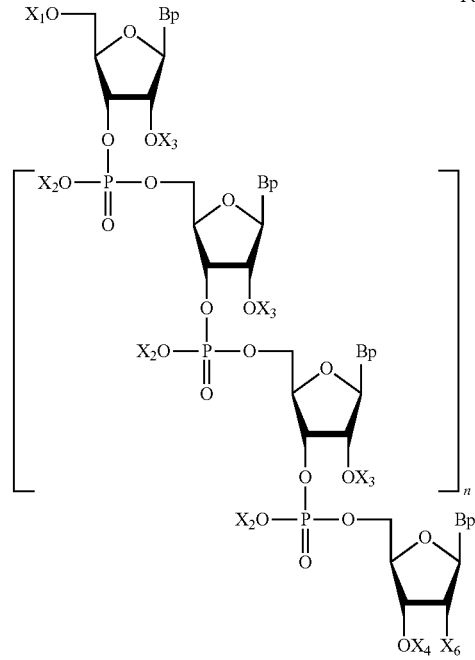

Formula I in which:

X$_1$ is H or a hydroxyl-protecting group selected from a dimethoxytrityl group, a monomethoxytrityl group and a pixyl group, preferably a dimethoxytrityl group, X$_2$ is H or a group protecting the phosphate that is β-removable, preferably a cyanoethyl group, X$_3$ is a base-labile group protecting the hydroxyls in position 2' of the ribose of the following formula A:

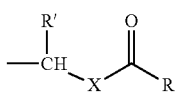

Formula A in which X is O or S, R' is H or CH$_3$, and R is selected from a linear or branched C$_1$ to C$_4$ alkyl group and a group R$_1$—O—R$_2$ in which R$_1$ is a C$_1$ to C$_2$ alkyl group and R$_2$ is a CH$_3$ or CH$_2$CH$_2$—O—CH$_3$ or aryl group.

X$_4$ represents the linker-solid substrate assembly,

X$_6$ is H or OX$_3$ or OAc,

Bp is a nucleic acid base: thymine, natural or modified when X$_6$ is H; uracil, natural or modified when X$_6$ is OX$_3$ or OAc; adenine, natural or modified and protected; cytosine, natural or modified and protected, or guanine, natural or modified and protected regardless of X$_6$, and n is an integer greater than or equal to 0, characterized in that it comprises a step a) of treatment of the protected single-stranded RNA bound to a substrate of formula I with a base selected from piperidine, 1,8-diazabicyclo[5.4.0]undec-7-ene (DBU), and triethylamine, at room temperature, for releasing the phosphates from the 3'-5' internucleotide linkers when X$_2$ is different from H, followed by a step b) of treatment of the RNA partially liberated obtained in step a), with a base selected from concentrated ammonia, methylamine, potassium carbonate, at room temperature.

Preferably, in formula I, X$_3$ is a group of formula A.

More preferably, in formula I, X$_3$ is selected from a pivaloyloxymethyl group, an isobutyryloxymethyl group, an n-butyryloxymethyl group, a propionyloxymethyl group and an acetyloxymethyl group.

In a first preferred embodiment of the method of release of the invention, in formula I, the nucleic acid base Bp is natural or modified uracil.

In a second preferred embodiment of the method of release of the invention, in formula I, the four nucleic acid bases uracil, adenine, cytosine and guanine, natural or modified optionally and independently of one another, are present, and in step b), removal of the X$_3$ group is carried out preferably by treatment with a 28% aqueous ammonia solution and then addition of 15% by volume, relative to the volume of ammonia, of isopropylamine and then evaporation under reduced pressure.

In a third preferred embodiment of the method of release of the invention, the protected RNA, bound to a substrate of formula I, is bound to a solid substrate by a base-labile linker.

In a fourth preferred embodiment of the method of release of the invention, in formula I, the four nucleic acid bases, natural or optionally modified, independently of one another, thymine, adenine, cytosine, and guanine are present when X$_6$ is H.

The invention also proposes a method of synthesis of a single-stranded RNA. characterized in that it comprises the following steps:

a) binding, to a substrate, by a linker, of a monomer of the following formula II

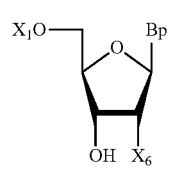

Formula II in which:

Bp is a natural or modified nucleic acid base, said nucleic acid base being a uracil nucleic acid base when X$_6$ is OX$_3$ or OAc, or a thymine nucleic acid base when X$_6$ is H, or a protected adenine nucleic acid base or a protected cytosine nucleic acid base or a protected guanine nucleic acid base, regardless of X$_6$ X$_1$ is a dimethoxytrityl group, X$_6$ is H or a group OAc or OX$_3$ in which X$_3$ is a group of the following formula A:

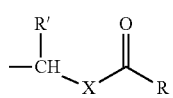

Formula A in which X is O or S, R' is H or CH$_3$, and R is selected from a linear or branched C$_1$ to C$_4$ alkyl group and a group R$_1$—O—R$_2$ in which R$_1$ is a C$_1$ to C$_2$ alkyl group and R$_2$ is a CH$_3$ or CH$_2$CH$_2$—O—CH$_3$ or aryl group, b) assembly of the monomer of formula II bound to its substrate obtained in step a) with at least one monomer of the following formula III:

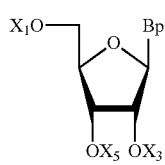

Formula III in which X$_1$, Bp, and X$_3$ are as defined for formula II and X$_5$ is a hydrogen phosphonate monoester group or phosphoroamidite, preferably a 2-cyanoethyl-N,N-diisopropylphosphoroamidite group, by which a protected single-stranded RNA is obtained bound to a substrate of formula I, c) optionally, treatment of the assembly obtained in step b) with an acid medium, and d) release of the protected single-stranded RNA bound to a substrate obtained in step b) or in step c), by the method of release of the invention.

The invention also proposes a method of synthesis of a double-stranded RNA, characterized in that it comprises the synthesis of a single-stranded RNA according to the method of synthesis of single-stranded RNA of the invention, and the hybridization of this single-stranded RNA thus synthesized to a single-stranded RNA having a complementary sequence.

Preferably, the double-stranded RNA is an siRNA.

However, the invention further proposes a method of synthesis of a monomer of the following formula III:

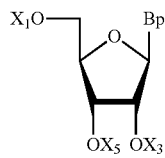

Formula III in which $X_1$, Bp, $X_3$ are as defined for formula II and $X_5$ is a hydrogen phosphonate or phosphoroamidite group, preferably a 2-cyanoethyl-N,N-diisopropylphosphoroamidite group, by which a protected single-stranded RNA is obtained on a support of formula I, from a ribonucleoside monomer of the following formula IV:

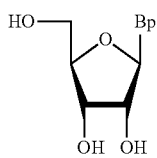

Formula IV in which Bp is as defined for formula II, characterized in that it consists of the following steps:

a) protection of the exocyclic amines of the nucleic acid bases Bp, when the nucleic acid base Bp is different from uracil, optionally modified, b) protection of the hydroxyl in position 5' of the ribose sugar, c) protection of the hydroxyl in position 2' of the ribose sugar with a group of the following formula A, and

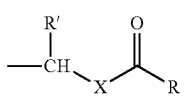

Formula A in which X is O or S, R' is H or $CH_3$, and R is selected from a linear or branched $C_1$ to $C_4$ alkyl group and a group $R_1$—O—$R_2$ in which $R_1$ is a $C_1$ to $C_2$ alkyl group and $R_2$ is a $CH_3$ or $CH_2CH_2$—O—$CH_3$ or aryl group, d) functionalization of the hydroxyl in position 3' of the ribose sugar with a hydrogen phosphonate monoester group or phosphoroamidite, preferably a 2-cyanoethyl-N,N-diisopropylphosphoroamidite group.

More preferably, in step c), the group of formula A is a pivaloyloxymethyl group or an isobutyryloxymethyl group or an n-butyryloxymethyl group, or a propionyloxymethyl group or an acetyloxymethyl group.

Also preferably, in step b), the protecting group is a dimethoxytrityl group.

In a first preferred embodiment of the method of synthesis of the monomer of formula III according to the invention, the nucleic acid base is cytosine, natural or modified, and the protecting group in step a) is an acetyl group.

In a second preferred embodiment of the method of synthesis of the monomer of formula III according to the invention, the nucleic acid base is adenine, natural or modified, and the protecting group in step a) is a phenoxyacetyl group.

In a third preferred embodiment of the method of synthesis of the monomer of formula III according to the invention, the nucleic acid base is guanine, natural or modified, and the protecting group in step a) is a tert-butylphenoxyacetyl or isopropyl phenoxyacetyl group.

The invention will be better understood and other advantages and characteristics thereof will become clearer on reading the explanatory description that now follows.

In the invention, the terms "nucleic acid base(s) Bp" or "Bp" denote a uracil, adenine, cytosine or guanine nucleic acid base, optionally modified, protected or unprotected, as will be clear to a person skilled in the art.

DETAILED DESCRIPTION OF THE INVENTION

The invention represents a break from the previous strategies of RNA synthesis, regardless of the number of ribonucleotide units of which it is composed, and whether these ribonucleotide units are natural or modified units, by the chemical route, in that it uses groups that protect the various reactive functions on the ribonucleotides, including in particular groups protecting the phosphates of the 3'-5 internucleotide linkers, when using the route of synthesis with phosphoroamidites, and groups protecting the hydroxyls in position 2' of the ribose rings, which are removed in basic conditions, at the end of elongation of the RNA. This makes it possible, when the groups protecting the nucleic acid bases, when present, and the linker binding the protected synthesized RNA to the substrate are also base-labile, to use a strategy of RNA synthesis that is entirely base-labile. The invention is therefore a break from the dogma "RNA synthesis is incompatible with a strategy that is entirely base-labile".

The key characteristic making it possible to use such a strategy that is entirely base-labile, is the use, for protecting the hydroxyl in position 2' of the ribose sugar, of protecting groups of the following formula A:

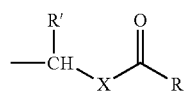

Formula A in which X is O or S, R' is H or $CH_3$, and R is selected from a linear or branched $C_1$ to $C_4$ alkyl group and a group $R_1$—O—$R_2$ in which $R_1$ is a $C_1$ to $C_2$ alkyl group and $R_2$ is a $CH_3$ or $CH_2CH_2$—O—$CH_3$ or aryl group.

More preferably, these protecting groups of formula A are pivaloyloxymethyl or isobutyryloxymethyl or butyryloxymethyl or propionyloxymethyl or acetyloxymethyl groups.

In fact, using said protecting groups makes it possible to liberate the hydroxyls in position 2' of the ribose of the desired RNA by a treatment with a base, without rupture of the RNA and without contamination by the fluoride salts used in the prior art.

The pivaloyloxymethyl, acetyloxymethyl, pivaloylthiomethyl, and acetylthiomethyl protecting groups have already been introduced in position 2' of the ribose ring, forming with the OH in position 2' of the ribose ring, an O-pivaloyloxymethyl, O-acetyloxymethyl, O-pivaloylthiomethyl or O-acetylthiomethyl group, respectively, with the aim of improving certain properties of the protected RNA, in particular its permeability to cell membranes, and its resistance to nucleases, as described in Parey et al., "*First Evaluation of*

Acyloxymethyl or Acylthiomethyl Groups as Biolabile 2'-O-Protections of RNA", Organic Letters, 2006, Vol. 8, No. 17, 3869-3872.

In this article, acetal ester groups, and in particular pivaloyloxymethyl, acetyloxymethyl, pivaloylthiomethyl and acetylthiomethyl groups, are described as groups that can enable the RNA thus functionalized in position 2' of the ribose ring, to cross the cell membrane and then be deprotected by the cell itself with its content of enzymes. These protecting groups were therefore described as biolabile groups and nothing in this document suggests that the use of such protecting groups would make it possible to use a strategy of RNA synthesis with base-labile protections that are deprotected in basic conditions.

Moreover, in this document, the selective introduction of the acetal ester group in position 2' of the ribonucleoside monomer is performed by a synthesis in which Markiewicz reagent (TlPSiCl$_2$) simultaneously blocks the hydroxyls in positions 5' and 3' of the ribose and leaves the hydroxyl at 2' of the ribose free to accept the pivaloyloxymethyl, acetyloxymethyl, pivaloylthiomethyl or acetylthiomethyl group, depending on the group selected. This method makes it possible to avoid the production and separation of the different protected isomers 2' and 3' but it requires at least seven steps for the synthesis of the protected RNA.

Although these seven steps take place with high yields, they are time-consuming and TlPSiCl$_2$ is an expensive reagent.

The invention, in contrast, proposes a method of synthesis of the ribonucleoside monomer in which the nucleic acid base, and the hydroxyls in position 3' and 5' of the ribose are protected entirely conventionally, the hydroxyl in position 2' of the ribose sugar being protected by an acyloxyalkyl or acylthioalkyl group, preferably acyloxymethyl, which takes place in four steps with a final yield between 27% and 37%.

This method starts, as in the prior art, from the compounds of the following formula IV:

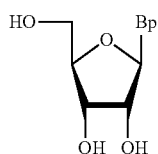

Formula IV in which Bp is a natural or modified nucleic acid base, uracil, adenine, cytosine, or guanine.

The first step of this method consists of protecting the nucleic acid base, when the latter is different from uracil.

The second step consists of protecting the hydroxyl in position 5' of the ribose ring with a protecting group classically used by a person skilled in the art for this purpose. These protecting groups used conventionally for protecting the hydroxyl in position 5' of the ribose ring are, among others, the dimethoxytrityl, monomethoxytrityl and pixyl groups.

In the invention, the preferred protecting group used is an acid-labile dimethoxytrityl group, widely used in oligonucleotide synthesis.

The third step of the method of synthesis of a ribonucleotide monomer, which serves as a building block for assembling a chain leading to the production of a single-stranded RNA, is protection of the hydroxyl in position 2' of the ribose by a group of the following formula A:

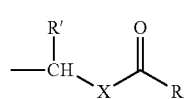

Formula A in which X is O or S, R' is H or CH$_3$, and R is selected from a linear or branched C$_1$ to C$_4$ alkyl group and a group R$_1$—O—R$_2$ in which R$_1$ is a C$_1$ to C$_2$ alkyl group and R$_2$ is a CH$_3$ or CH$_2$CH$_2$—O—CH$_3$ or aryl group.

More preferably, the group protecting the hydroxyl in position 2' of the ribose is a pivaloyloxymethyl group or an isobutyryloxymethyl group, or an n-butyryloxymethyl group, or a propionyloxymethyl group, or an acetyloxymethyl group.

Most preferably, the group protecting the hydroxyl in position 2' of the ribose is a pivaloyloxymethyl group.

In this step, two isomers are obtained: one with the hydroxyl group in position 3' of the natural or modified ribose protected by the group of formula A, and the other with the hydroxyl group in position 2' of the natural or modified ribose protected by the group of formula A.

The isomer, whose hydroxyl in position 2' of the ribose ring is protected, is separated and the fourth step of the method of synthesis of the protected ribonucleotide monomer according to the invention then consists of functionalizing the hydroxyl in position 3' of the ribose by a phosphorylated group well known by a person skilled in the art. Preferably, in a first embodiment, a phosphoroamidite group is used in the method of the invention, more preferably a 2-cyanoethyl-N,N-diisopropylphosphoroamidite group.

The compound of the following formula III is then obtained:

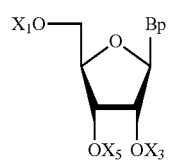

Formula III in which:
Bp is a natural or modified nucleic acid base, uracil or a protected adenine nucleic acid base or a protected cytosine nucleic acid base or a protected guanine nucleic acid base,
X$_1$ is a hydroxyl-protecting group, selected from acid-labile groups and preferably the dimethoxytrityl group,
X$_5$ is a phosphoroamidite group, preferably a 2-cyanoethyl-N,N-diisopropylphosphoroamidite group,
X$_3$ is a group of formula A as defined previously.

However, in a second embodiment, a hydrogen phosphonate monoester group is used in the method of the invention for functionalization of the hydroxyl in position 3'.

The compound of formula III that is then obtained is a compound of formula III in which Bp, X$_1$, and X$_3$ are as defined previously but X$_5$ is a hydrogen phosphonate monoester group.

Starting from the ribonucleotide monomers of formula III and the ribonucleotide monomer of formula II in which X$_6$ is OX$_3$ or OAc or the deoxyribonucleotide of formula II in which X$_6$ is H, a protected single-stranded RNA is synthesized on a solid substrate.

The method of synthesis of this protected single-stranded RNA is also an object of the invention.

This protected single-stranded RNA has the following formula I:

Formula I

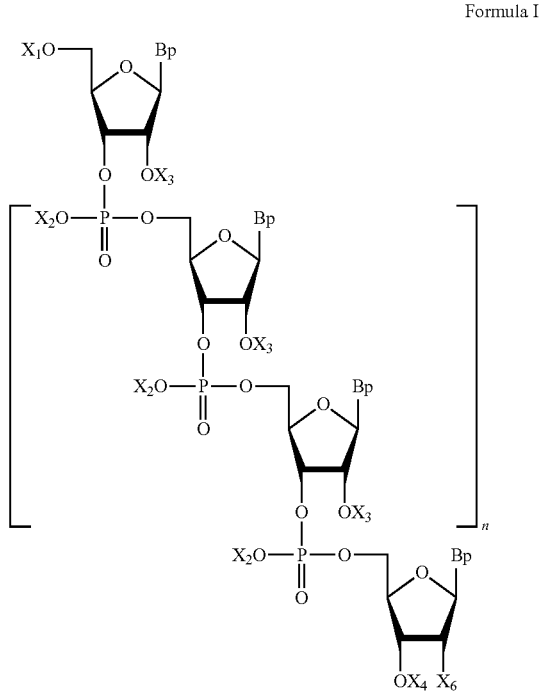

in which:

$X_1$ is H or a hydroxyl-protecting group selected from acid-labile groups and preferably a dimethoxytrityl group, $X_2$ is H or a group protecting the phosphate, preferably a 2-cyanoethyl group, $X_3$ is a group of the following formula A:

Formula A

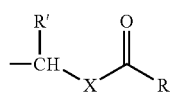

in which X is O or S, R' is H or $CH_3$, and R is selected from a linear or branched $C_1$ to $C_4$ alkyl group and a group $R_1$—O—$R_2$ in which $R_1$ is a $C_1$ to $C_2$ alkyl group and $R_2$ is a $CH_3$ or $CH_2CH_2$—O—$CH_3$ or aryl group, $X_4$ represents the assemblage of the solid substrate and of the linker that joins the oligonucleotide to the substrate. The substrate can be glass beads (LCA-CPG: long chain alkylamine-controlled pore glass) or beads of polystyrene resin (HCP: highly crosslinked polystyrene). The linker is selected from linkers broken by a base at the end of elongation such as oxalyl, succinyl, glyoxal, hydroquinone-O,O-diacetic acid (Q-linker) and preferably the succinyl linker or Q-linker, $X_6$ is H or a group $OX_3$ or OAc, Bp is a natural or modified nucleic acid base, thymine when $X_6$ is H or uracil when $X_6$ is $OX_3$ or OAc or protected adenine, or protected cytosine, or protected guanine, regardless of $X_6$, and, n is an integer greater than or equal to 0.

When $X_6$ is OAc, the positions of $X_4$ and $X_6$ are interchangeable.

The method of synthesis according to the invention of this single-stranded RNA comprises a step of binding a ribonucleoside or deoxyribonucleoside monomer of formula II to a substrate as defined previously, by means of a linker which itself is preferably also base-labile, followed by a step of assembly of said monomer of formula II with at least one monomer of formula III, and optionally a step of acid treatment of the assembly of monomers obtained to remove the protecting group $X_1$, and finally a step of release of the protected RNA thus obtained.

Thus, the RNA to which the step of release is applied is either an RNA of formula I in which $X_1$ is H when the step of acid treatment is carried out, or an RNA of formula I in which $X_1$ is a hydroxyl-protecting group when the step of acid treatment is not carried out.

Assembly of the ribonucleotide monomers of formula III is generally carried out by automated synthesis on a solid substrate.

In this case, the synthesized protected RNA is bound, by its end $X_4$ in position 3', by a linker to the solid substrate.

When this linker is also base-labile, release of the RNA from its substrate is effected, in the method of the invention, at the same time as deprotection of the OH in position 2' of the ribose, and without an additional step.

This is true of any base-labile linker.

Once the single-stranded RNA has been released, a double-stranded RNA can then be formed by hybridization of the released single-stranded RNA to a single-stranded RNA having a complementary sequence. The single-stranded RNA having a complementary sequence can itself also have been synthesized by the method of the invention, or can have been synthesized by another method.

This makes it possible in particular to make siRNAs.

The method of release of the protected single-stranded RNA of formula I is an object of the invention. This method overcomes a prejudice of the prior art in that it consists of removing the protecting groups of the hydroxyls in position 2' of the ribose by a basic treatment.

More precisely, this basic treatment comprises a step a) of treatment of the protected RNA of formula I with a strong base selected from piperidine, 1,8-diazabicyclo[5.4.0]undec-7-ene (DBU), triethylamine, at room temperature, for releasing the phosphate of the 3'-5' internucleotide linkers.

This step a) is only carried out when the route of synthesis with phosphoroamidites is used.

In fact, when the route of synthesis with hydrogen phosphonates is used, assembly of the monomers results in hydrogen phosphonate diester 3'-5' internucleoside linkers being obtained, which are then oxidized to phosphates to obtain an RNA, which will then need to be released by the method of the invention, of formula I in which $X_2$ is H.

This optional step a) is followed by a step b) of treatment of the RNA thus partially released obtained in step a), with a strong base selected from concentrated ammonia, methylamine, potassium carbonate at room temperature.

Step b) is common for release of the RNA whatever route of RNA synthesis is used.

The treatment with piperidine or DBU at room temperature is carried out in any suitable solvent known by a person skilled in the art, and more preferably in THF or dry acetonitrile, for 15 minutes (piperidine) or 45 minutes (DBU 0.45M) or 1 minute (DBU 1 M).

After this deprotection of the phosphate of the 3'-5' internucleotide linker, the pivaloyloxymethyl, isobutyryloxymethyl, n-butyryloxymethyl, propionyloxymethyl, acetyloxymethyl protecting groups, depending on the group used, are still in place.

Then the hydroxyl groups in position 2' are released by treatment with concentrated aqueous ammonia, at room temperature, for 3 h. No rupture of the RNAs occurs in this step. This sequential deprotection in two steps first with DBU or piperidine then with aqueous ammonia is necessary to avoid attack by released hydroxyls in position 2', of the adjacent phosphotriesters or phosphodiesters, which could lead to chain breakage.

However, when the protected RNA of formula I contains the natural or modified nucleic acid bases: thymine or uracil, adenine, cytosine and guanine, i.e. at least four monomers of formula III in which the nucleic acid bases are all different, the method of release of the invention additionally comprises a step of addition of 15% of isopropylamine after the treatment with ammonia.

In all cases, the deprotection medium is evaporated under reduced pressure, to obtain the pure released RNA.

For better understanding of the invention, several embodiments will now be described, as examples that are purely for purposes of illustration and are nonlimiting.

In the examples given below, the ribonucleotide monomers of formula III where $X_5$ is a phosphoroamidite group, preferably a 2-cyanoethyl-N,N-diisopropylphosphoroamidite group, were synthesized according to the following general scheme:

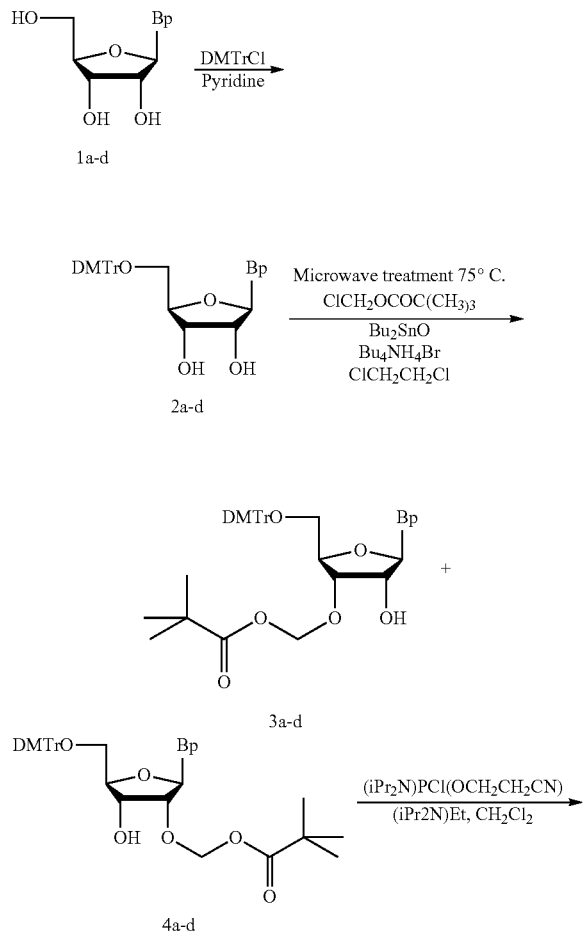

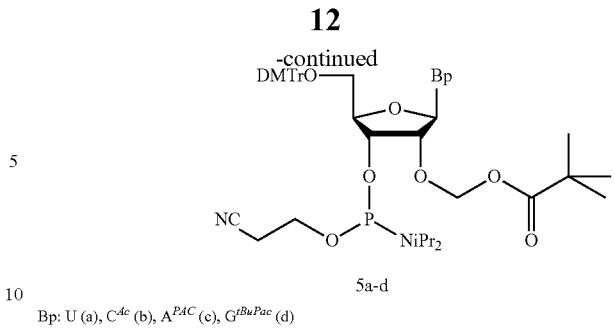

Bp: U (a), $C^{Ac}$ (b), $A^{PAC}$ (c), $G^{iBuPac}$ (d)

The first step of protection of the bases guanine, cytosine and adenosine is not shown in this scheme.

In this scheme, Bp can also be $G^{iPrPAC}$, in which case the step of introduction of the pivaloyloxymethyl group in position 2' of compound 2a-d is carried out without microwave treatment, as will be explained below.

Example 1

Synthesis of the monomer 2'-O-pivaloyloxymethyl-5'-O-(4,4'-dimethoxytrityl)uridine-3'-O-(2-cyanoethyl-N,N-diisopropylphosphoroamidite 5a The monomer synthesized here has formula III, in which the nucleic acid base is a uracil nucleic acid base, the group protecting the hydroxyl in position 5' of the ribose is dimethoxytrityl, the group grafted on the hydroxyl in position 3' of the ribose is 2-cyanoethyl-N,N-diisopropylphosphoroamidite, and the group protecting the hydroxyl in position 2' of the ribose is pivaloyloxymethyl.

For this synthesis, we start from 5'-O-(4,4'-dimethoxytrityl)uridine 2a. Therefore all that is left to be done is to introduce, in a first step, the pivaloyloxymethyl group in position 2' of the ribose and the 2-cyanoethyl-N,N-diisopropylphosphoroamidite group in position 3' of the monomer.

For this, the pivaloyloxymethyl group is introduced first in position 2' of the ribose.

More precisely, tetrabutylammonium bromide (1.93 g, 5.98 mmol, 1.3 eq), dibutyltin oxide (1.5 g, 5.98 mmol, 1.3 eq) and chloromethyl pivalate (1.67 mL, 11.5 mmol, 2.5 eq) are added to a solution of 5'-O-(4,4'-dimethoxytrityl)uridine 2a (2.5 g, 4.6 mmol, 1 eq) in dichloroethane (DCE) (15 mL).

The reaction mixture is heated under microwave radiation (power 300 W) at 75° C. for 2.5 h, cooled, and the solvent is evaporated.

Then, the reaction mixture is submitted to silica gel chromatography with a gradient of acetone (0-40%) in dichloromethane. The isomer eluting first is the desired compound 4a. It is obtained in the form of white foam after evaporation of the solvent.

Yield of 4a: 1.1 g, 36%

$^1$H NMR (300 MHz, HH—COSY, CDCl$_3$): δ 9.57 (s, 1H, NH); 7.94 (d, $J_{H-6/H-5}$=8.1 Hz, 1H, H-6); 7.37-7.09 (m, 9H, H ar, DMTr); 6.83-6.69 (m, 4H, H ar, DMTr); 5.87 (d, $^3J_{H1'/H2'}$=1.8 Hz, 1H, H-1'); 5.52, 5.37 (2d$_{AB}$, $J_{AB}$=6.3 Hz, 1H+1H, OCH$_2$O); 5.23 (d, $J_{H-5/H-6}$=8.1 Hz, 1H, H-5); 4.39 (ddd, $^3J_{H3'/OH3'}$=8.8 Hz; $^3J_{H3'/H4'}$=7.7 Hz; $^3J_{H3'/H2'}$=5.2 Hz, 1H, H-3'); 4.24 (dd, $^3J_{H2'/H3'}$=5.2 Hz; $^3J_{H2'/H1'}$=1.8 Hz, 1H, H-2'); 3.95 (dt, $^3J_{H4'/H3'}$=7.7 Hz; $^3J_{H4'H5'\_H5''}$=2.1 Hz, 1H, H-4'); 3.71 (s, 6H, 2 OCH$_3$); 3.48 (dd, $^2J_{H5'/H5''}$=11.2 Hz; $^3J_{H5'/H4'}$=2.1 Hz, 1H, H-5'); 3.42 (dd, $^2J_{H5''/H5'}$=11.2 Hz; $^3J_{H5''/H4'}$=2.1 Hz, 1H, H-5''); 2.48 (d, $J_{OH-3'/H-3'}$=8.8 Hz, 1H, OH$_3'$); 1.15 (s, 9H, OCOC(CH$_3$)$_3$).

$^{13}$C NMR (75 MHz, CDCl$_3$): δ 177.1 (OC=O); 162.5 (C=O); 157.7; 157.6; 143.3; 134.2; 133.9 (Cq, Car); 149.2 (C=O); 138.8 (C$_6$); 129.2; 129.1; 127.1; 127.0; 126.2; 112.3 (CH, Car); 101.2 (C$_5$); 87.2 (C$_{1'}$); 86.9 (OCH$_2$O); 86.1 (OCq, DMTr); 82.2 (C$_{4'}$); 81.1 (C$_{2'}$); 67.5 (C$_{3'}$); 60.1 (C$_{5'}$); 54.2 (OCH$_3$, DMTr); 37.8 (Cq, OCOC(CH$_3$)$_3$); 25.9 (OCOC(CH$_3$)$_3$). HRMS (FAB) calculated for: C$_{36}$H$_{40}$N$_2$O$_{10}$ [M+H]$^+$ 660.2709. Found: 660.2683.

Starting from the 2'-O-pivaloyloxymethyl-5'-O-(4,4'-dimethoxytrityl)uridine 4a thus obtained, 2'-O-pivaloyloxymethyl-5'-O-(4,4'-dimethoxytrityl)uridine 3'-O-(2-cyanoethyl-N,N-diisopropylphosphoroamidite 5a was obtained as follows:

The 2'-O-pivaloyloxymethyl-5'-O-(4,4'-dimethoxytrityl) uridine obtained in the preceding step 4a (1 g, 1.51 mmol, 1 eq) is dried by coevaporation three times with anhydrous CH$_3$CN. Then the residue is dissolved in anhydrous CH$_2$Cl$_2$ (10 mL) and a mixture of N,N-diisopropylethylamine (474 μL, 2.72 mmol, 1.8 eq), 2-cyanoethyl-N,N-diisopropylchlorophosphoroamidite (506 μL, 2.27 mmol, 1.5 eq) and CH$_2$Cl$_2$ (1 mL) is added dropwise. The mixture is stirred under argon at room temperature for 3 h.

Next, ethyl acetate is added, the reaction mixture is poured into saturated NaHCO$_3$ solution and extractions with EtOAc are performed. The mixture obtained after drying the extract over Na$_2$SO$_4$, and removal of the solvent, is purified by silica gel chromatography with a gradient of CH$_2$Cl$_2$ (60-100%) in cyclohexane with 1% of pyridine. The desired monomer of formula III, 5a, is obtained. It is in the form of white foam, after evaporation of the solvent.

Yield of 5a: 1.05 g, 81%.

$^{31}$P NMR (121 MHz, CD$_3$CN): δ 150.35; 149.20.

Example 2

Synthesis of N$^4$-acetyl-2'-O-pivaloxyoxymethyl-5'-O-(4,4'-dimethoxytrityl)cytidine-3'-O-(2-cyanoethyl-N,N-diisopropyl phosphoroamidite 5b This ribonucleotide monomer of formula III is the monomer in which the nucleic acid base is cytosine, the group protecting the hydroxyl in position 5' of the ribose is dimethoxytrityl, the group grafted on the hydroxyl in position 3' of the ribose is 2-cyanoethyl-N,N-diisopropylphosphoroamidite and the group protecting the hydroxyl in position 2' of the ribose is pivaloyloxymethyl.

In this synthesis we start from N$^4$-acetyl-5'-O-(4,4'-dimethoxytrityl) cytidine 2b, which indicates that this example describes the protection of the OH groups in position 2' and 3' of the ribose.

These protections were carried out in the following way:

Tetrabutylammonium bromide (1.78 g, 5.54 mmol, 1.3 eq), dibutyltin oxide (1.39 g, 5.54 mmol, 1.3 eq), and chloromethyl pivalate (1.55 mL, 10.65 mmol, 2.5 eq) are added to a solution of N$^4$-acetyl-5'-O-(4,4'-dimethoxytrityl)cytidine 2b (2.5 g, 4.26 mmol, 1 eq) in DCE (15 mL). The reaction mixture is heated under microwave radiation (power 300 W) at 75° C. for 2.5 h, cooled, and the solvent is evaporated.

The reaction mixture is submitted to silica gel chromatography with a gradient of acetone (40-100%) in dichloromethane.

The isomer eluting first is the desired compound 4b, which is obtained in the form of white foam after evaporation of the solvent.

Yield of 4b: 1.14 g, 38%.

$^1$H NMR (400 MHz, HH—COSY, CDCl$_3$): δ 9.84 (s, 1H, NH); 8.42 (d, J$_{H-6/H-5}$=7.5 Hz, 1H, H-6); 7.34-7.14 (m, 9H, H ar, DMTr); 7.06 (d, J$_{H-5/H-6}$=7.5 Hz, 1H, H-5); 6.80-6.76 (m, 4H, H ar, DMTr); 5.86 (s, 1H, H-1'); 5.60; 5.50 (2d$_{AB}$, J$_{AB}$=6.1 Hz, 1H+1H, OCH$_2$O); 4.34 (dt, $^3$J$_{H3'/OH3'}$=10.6 Hz; $^3$J$_{H3'/H4',H2'}$=5.2 Hz, 1H, H-3'); 4.21 (d, $^3$J$_{H2'/H3'}$=5.2 Hz, 1H, H-2'); 3.98 (dt, $^3$J$_{H4'/H3'}$=5.2 Hz; $^3$J$_{H4'/H5',H5''}$=1.9 Hz, 1H, H-4'); 3.71 (s, 6H, 2 OCH$_3$); 3.52 (dd, $^2$J$_{H5'/H5''}$=11.1 Hz; $^3$J$_{H5'/H4'}$=1.9 Hz, 1H, H-5'); 3.48 (dd, $^2$J$_{H5''/H5'}$=11.1 Hz; $^3$J$_{H5''/H4'}$=1.9 Hz, 1H, H-5''); 2.50 (d, J$_{OH-3'/H-3'}$=10.6 Hz, 1H, OH$_3$'); 2.19 (s, 3H, NHCOCH$_3$); 1.13 (s, 9H, OCOC(CH$_3$)$_3$).

$^{13}$C NMR (100 MHz, CDCl$_3$): δ 178.2 (OC=O); 170.6 (NHCO); 163.1 (C$_4$); 158.7 (Cq, Car); 147.4 (C$_2$); 146.6 (C$_6$); 146.3; 135.2 (Cq, Car); 130.1; 129.2; 128.2; 128; 127.9; 127.8; 127.2; 127; 113.3; 113.1 (CH, Car); 96.8 (C$_5$); 91.5 (C$_{1'}$); 88.0 (OCH$_2$O); 87.6 (OCq, DMTr); 83.1 (C$_{4'}$); 81.7 (C$_{2'}$); 67.8 (C$_{3'}$); 60.7 (C$_{5'}$); 55.3 (OCH$_3$, DMTr); 38.9 (Cq, OCOC(CH$_3$)$_3$); 27.0 (OCOC(CH$_3$)$_3$); 18.1 (COCH$_3$). HRMS (FAB) calculated for C$_{38}$H$_{44}$N$_3$O$_{10}$ [M+H]$^+$: 702.3042. Found: 702.3027.

Then, 1.3 g, 1.85 mmol, 1 eq of the compound thus obtained 4b is dried by coevaporation three times with anhydrous CH$_3$CN. The residue obtained is dissolved in anhydrous CH$_2$Cl$_2$ (13 mL) and a mixture of N,N-diisopropylethylamine (580 μL, 3.33 mmol, 1.8 eq) 2-cyanoethyl-N,N-diisopropylchlorophosphoroamidite (620 μL, 2, 78 mmol, 1.5 eq) and CH$_2$Cl$_2$ (1 mL) is added dropwise. The mixture is stirred under argon at room temperature for 3 h. Next, ethyl acetate is added, the reaction mixture is poured into saturated NaHCO$_3$ solution and extractions with EtOAc are performed. The mixture obtained after drying the extract over Na$_2$SO$_4$, and removal of the solvent, is purified by silica gel chromatography with a gradient of EtOAc (10-80%) in hexane with 1% of pyridine.

The desired ribonucleotide monomer of formula III, 5b, is obtained in the form of white foam after evaporation of the solvent.

Yield of 5b: 1.37 g, 82%.

$^{31}$P NMR (121 MHz, CD$_3$CN): δ 150.15; 148.35.

Example 3

Synthesis of N$^6$-phenoxyacetyl-2'-O-pivaloyloxymethyl-5'-O-(4,4'-dimethoxytrityl)adenosine 3'-O-(2-cyanoethyl-N,N-diisopropylphosphoroamidite) 5c This compound corresponds to the monomer of formula III in which the nucleic acid base is adenine, whose amine is protected by a phenoxyacetyl group, the group protecting the hydroxyl in position 5' of the ribose is dimethoxytrityl, the group grafted on the hydroxyl in position 3' is 2-cyanoethyl-N,N-diisopropylphosphoroamidite, and the group protecting the hydroxyl in position 2' of the ribose is pivaloyloxymethyl.

For this synthesis, we start from the ribonucleoside 2c, in which the nucleic acid base and the hydroxyl in position 5' are protected.

Tetrabutylammonium bromide (596 mg, 1.85 mmol, 1.3 eq), dibutyltin oxide (462 mg, 1.85 mmol, 1.3 eq) and chloromethyl pivalate (515 μL, 3.55 mmol, 2.5 eq) are added to a solution of N$^6$-phenoxyacetyl-5'-O-(4,4'-dimethoxytrityl) adenosine 2c (1 g, 1.42 mmol, 1 eq) in DCE (5 mL). The reaction mixture is heated under microwave radiation (power 300 W) at 75° C. for 2.5 h, cooled, and the solvent is evaporated. The reaction mixture is submitted to silica gel chromatography with a gradient of acetone (0-30%) in dichloromethane. The isomer eluting first is the desired compound 4c, in the form of white foam after evaporation of the solvent.

Yield of 4c: 395 mg, 34%.

$^1$H NMR (400 MHz, HH—COSY, CDCl$_3$): δ 9.50 (s, 1H, NH); 8.72 (s, 1H, H-2); 8.25 (s, 1H, H-8); 7.44-6.81 (m, 18H, H ar, DMTr-Pac); 6.22 (d, $^3J_{H1'/H2'}$=4.7 Hz, 1H, H-1'); 5.51; 5.40 (2d$_{AB}$, J$_{AB}$=5.8 Hz, 1H+1H, OCH$_2$O); 5.08 (t, $^3J_{H2'/H3'.H1'}$=4.7 Hz; 1H, H-2'); 4.88 (s, 2H, NHCOCH$_2$Ph); 4.55 (q, $^3J_{H3'/H2'.OH3'.H4'}$=4.7 Hz, 1H, H-3'); 4.28 (m, 1H, H-4'); 3.79 (s, 6H, 2 OCH$_3$); 3.54 (dd, $^2J_{H5'/H5'}$=10.7 Hz; $^3J_{H5'/H4'}$=3.3 Hz, 1H, H-5'); 3.43 (dd, $^2J_{H5''/H5'}$=10.7 Hz; $^3J_{H5''/H4'}$=4 Hz, 1H, H-5''); 2.75 (d, J$_{OH-3'/H-3'}$=4.7 Hz. 1H, OH$_3$'); 1.17 (s, 9H, OCOC(CH$_3$)$_3$).

$^{13}$C NMR (100 MHz, CDCl$_3$): δ 177.9 (OC=O); 166.7 (NHCO); 158.6 (Cq, Car); 157.2 (Cq, Pac); 152.6 (C$_2$); 151.5 (C$_6$); 148.4 (C$_4$); 144.4; 135.5 (Cq, Car); 142.2 (C$_8$); 130.1; 129.9; 128.1; 127.9; 122.4; 115; 114.9; 113.2 (CH, Car); 123.2 (C$_5$); 89.0 (OCH$_2$O); 87.3 (C$_{1'}$); 86.7 (OCq, DMTr); 84.2 (C$_{4'}$); 81.7 (C$_{2'}$); 70.5 (C$_{3'}$); 68.1 (NHCOCH$_2$Ph); 62.9 (C$_{5'}$); 55.3 (OCH$_3$, DMTr); 38.9 (Cq, OCOC(CH$_3$)$_3$); 27.0 (OCOC(CH$_3$)$_3$). HRMS (FAB) calculated for C$_{45}$H$_{48}$N$_5$O$_{10}$ [M+H]$^+$: 818.3401. Found: 818.3397.

The compound obtained 4c (550 mg, 0.67 mmol, 1 eq) is dried by coevaporation three times with anhydrous CH$_3$CN. Then the residue is dissolved in anhydrous CH$_2$Cl$_2$ (7 mL) and a mixture of N,N-diisopropylethylamine (211 μL, 1.21 mmol, 1.8 eq), 2-cyanoethyl-N,N-diisopropylchlorophosphoroamidite (223 μL, 1 mmol, 1.5 eq) and CH$_2$Cl$_2$ (0.5 mL) is added dropwise. The mixture is stirred under argon at room temperature for 2 h. Next, ethyl acetate is added, the reaction mixture is poured into a saturated solution of NaHCO$_3$ and extractions with EtOAc are performed.

The mixture obtained after drying the extract over Na$_2$SO$_4$ and removal of the solvent is purified by silica gel chromatography with a gradient of CH$_2$Cl$_2$ (40-100%) in cyclohexane with 1% of pyridine. The desired ribonucleotide monomer 5c is obtained in the form of white foam after evaporation of the solvent.

Yield of 5c: 540 mg, 79%.

$^{31}$P NMR (121 MHz, CDCl$_3$): δ150.85; 150.80.

Example 4

Synthesis of N$^2$-tert-butylphenoxyacetyl-2'-O-pivaloyloxymethyl-5'-O-(4,4'-dimethoxytrityl)guanosine 3'-O-(2-cyanoethyl-N,N-diisopropylphosphoroamidite) 5d The compound synthesized in this example is the monomer of formula III 5d in which the nucleic acid base is guanine protected by tert-butylphenoxyacetyl, the hydroxyl in position 5' is dimethoxytrityl, the group grafted on the hydroxyl in position 3' is 2-cyanoethyl-N,N-diisopropylphosphoroamidite, and the group protecting the hydroxyl in position 2' of the ribose is pivaloyloxymethyl.

In this case we start from the ribonucleoside 2d whose nucleic acid base as well as the hydroxyl group in position 5' of the ribose are protected.

Tetrabutylammonium bromide (1.4 g, 4.36 mmol, 1.3 eq), dibutyltin oxide (1.1 g, 4.36 mmol, 1.3 eq), and chloromethyl pivalate (1.22 mL, 8.38 mmol, 2.5 eq) are added to a solution of N$^2$-tert-butylphenoxyacetyl-5'-O-(4,4'-dimethoxytrityl) guanosine 2d (2.6 g, 3.35 mmol, 1 eq) in DCE (15 mL). The reaction mixture is heated under microwave radiation (power 300 W) at 75° C. for 2 h, cooled, and the solvent is evaporated. The reaction mixture is submitted to silica gel chromatography with a gradient of acetone (0-15%) in dichloromethane.

The isomer eluting first is the desired compound 4d which is obtained in the form of white foam after evaporation of the solvent.

Yield of 4d: 1.46 g, 49%.

$^1$H NMR (400 MHz, HH—COSY, CDCl$_3$): δ 11.78 (s, 1H, NH-1); 9.09 (s, 1H, NH$_{Pac}$); 7.79 (s, 1H, H-8); 7.36-6.73 (m, 18H, H ar, DMTr-tbuPac); 5.99 (d, $^3J_{H1'/H2'}$=4.7 Hz, 1H, H-1'); 5.46; 5.36 (2d$_{AB}$, J$_{AB}$=5.3 Hz, 1H+1H, OCH$_2$O); 5.23 (s, 2H, NHCOCH$_2$Ph); 4.65 (t, $^3J_{H2'/H3'.H1'}$=4.7 Hz; 1H, H-2'); 4.34 (m, 1H, H-3'); 4.17 (m, 1H, H-4'); 3.70 (s, 6H, 2 OCH$_3$); 3.38 (dd, $^2J_{H5'/H5'}$=10.7 Hz; $^3J_{H5'/H4'}$=2.7 Hz, 1H, H-5'); 3.35 (dd, $^2J_{H5''/H5'}$=10.7 Hz; $^3J_{H5''/H4'}$=2.9 Hz, 1H, H-5''); 2.49 (d, J$_{OH-3'/H-3'}$=4.3 Hz. 1H, OH$_3$'); 1.24 (s, 9H, OCOC(CH$_3$)$_3$); 1.10 (s, 9H, tbuPac).

$^{13}$C NMR (100 MHz, CDCl$_3$): δ 177.9 (OC=O); 169.9 (NHCO); 158.6 (Cq, Car); 155.2 (C$_6$); 154.2 (Cq, tbuPac); 147.7 (C$_2$); 146.5 (C$_4$); 145.9 (Cq, tbuPac); 144.3; 135.5 (Cq, Car); 137.0 (C$_8$); 130.1; 128.1; 127.1; 126.9; 126.8; 114.4; 113.3 (CH, Car); 122.3 (C$_5$); 89.3 (OCH$_2$O); 86.8 (OCq, DMTr); 86.1 (C$_{1'}$); 84.0 (C$_{2'}$); 82.7 (C$_{4'}$); 70.4 (C$_{3'}$); 67.1 (NHCOCH$_2$Ph); 63.1 (C$_{5'}$); 55.3 (OCH$_3$, DMTr); 38.9 (Cq, OCOC(CH$_3$)$_3$); 34.3 (Cq, PhC(CH$_3$)$_3$); 31.4 (PhC(CH$_3$)$_3$); 27 (OCOC(CH$_3$)$_3$). HRMS (ESI) calculated for C$_{49}$H$_{56}$N$_5$O$_{11}$ [M+H]$^+$: 890.3976. Found: 890.3934.

The compound obtained 4d (700 mg, 0.79 mmol, 1 eq.) is dried by coevaporation three times with anhydrous CH$_3$CN. Then the residue is dissolved in anhydrous CH$_2$Cl$_2$ (5 mL) and a mixture of N,N-diisopropylethylamine (247 μL, 1.42 mmol, 1.8 eq.), 2-cyanoethyl-N,N-diisopropylchlorophosphoroamidite (265 μL, 1.19 mmol, 1.5 eq.) and CH$_2$Cl$_2$ (0.5 mL) is added dropwise. The mixture is stirred under argon at room temperature for 3 h. Next, ethyl acetate is added, the reaction mixture is poured into a saturated solution of NaHCO$_3$ and extractions with EtOAc are performed.

The mixture obtained after drying the extract over Na$_2$SO$_4$ and removal of the solvent is purified by silica gel chromatography with a gradient of CH$_2$Cl$_2$ (40-100%) in cyclohexane with 1% of pyridine. The desired ribonucleotide monomer 5d is obtained in the form of white foam after evaporation of the solvent.

Yield of 5d: 646 mg, 75%.

$^{31}$P NMR (121 MHz, CD$_3$CN): δ 150.43, 149.67.

The method described in the preceding examples for obtaining compounds 4a-d, and corresponding to the reaction of introduction of the pivaloyloxymethyl group, involves the use of a microwave apparatus. Said use can be a hindrance to scaling-up for production of ribonucleotides and development of the methodology of RNA synthesis by the method of the invention. For this reason, the invention also proposes a method of synthesis of the aforementioned compounds 5 not including the use of microwaves. In this method, on the one hand, the nucleic acid base Bp is protected by a group iPrPAC and, on the other hand, the step of introduction of the pivaloyloxymethyl group to obtain the compounds 4 has been replaced with the following general procedure:

The nucleosides 2a-d are dissolved in DCE or anhydrous acetonitrile, then dibutyltin oxide (DBTO), then tetrabutylammonium bromide (TBAB) and then chloromethyl pivalate or iodomethyl pivalate, depending on the nature of the nucleoside, are added at room temperature, with stirring and under argon. The reaction mixture is then heated and maintained at 70° C. or 75° C. under argon for a time varying from 1.5 h to 6 h.

For example, for the compounds in which Bp is G, the procedure is as follows:

Synthesis of the monomer 2'-O-pivaloyloxymethyl-5'-O-(4,4'-dimethoxytrityl) uridine 4a Nucleoside (1 eq), DBTO (1.3 eq), TBAB (1.3 eq), chloromethyl pivalate (2.5 eq) in acetonitrile at 70° C. for 3 h.

Synthesis of $N^4$-acetyl-2'-O-pivaloxyoxymethyl-5'-O-(4,4'-dimethoxytrityl) cytidine 4b Nucleoside (1 eq), DBTO (1.5 eq), TBAB (1.5 eq), chloromethyl pivalate (3 eq) in DCE at 75° C. for 6 h.

Synthesis of $N^6$-phenoxyacetyl-2'-O-pivaloyloxymethyl-5'-O-(4,4'-dimethoxytrityl) adenosine 4c Nucleoside (1 eq), DBTO (1.3 eq), TBAB (1.3 eq), iodomethyl pivalate (2.5 eq) in DCE at 70° C. for 1.5 h.

Synthesis of $N^2$-iso-propylphenoxyacetyl-2'-O-pivaloyloxymethyl-5'-O-(4,4'-dimethoxytrityl) guanosine 4e Compound 4e corresponds to compound 4d described in the general scheme but in which Bp is protected by the group iPrPAC.
Nucleoside (1 eq), DBTO (1.3 eq), TBAB (1.3 eq), chloromethyl pivalate (3 eq) in DCE at 75° C. for 3 h.

Example 5

Synthesis of Single-Stranded RNA of Formula I by Phosphoroamidite Chemistry with $X_3$ which is a Pivaloyloxymethyl Group Single-stranded RNAs were synthesized starting from the monomers 5a-d obtained in examples 1 to 4.

These protected RNAs of formula I were prepared in a DNA synthesizer, ABI model 381A, at a scale of 1 μmol, using the monomers 5a-d of formula III obtained in examples 1 to 4, in the conditions shown in Table 1 below.

TABLE 1

| Step | Operation | Reagent | Time (s) |
| --- | --- | --- | --- |
| 1 | Deblocking | 3% DCA in $CH_2Cl_2$ | 60 |
| 2 | Coupling | 0.1M amidite in $CH_3CN$ + 0.3M BMT in $CH_3CN$ | 180* |
| 3 | Masking | $(Pac)_2O$ in THF/pyridine + 10% NMI in THF | 200 |
| 4 | Oxidation | 0.1M $I_2$ in $THF/H_2O/Pyr$ | 20 |

DCA = dichloroacetic acid
BMT = benzylmercaptotetrazole
$(Pac)_2O$ = phenoxyacetic anhydride
NMI = N-methylimidazole A coupling time of 300 seconds was also applied for synthesis of the heteropolymers but did not significantly improve the coupling yield.

The protected RNAs ON1 to ON5 (SEQ ID NO:1 to SEQ ID NO:5) were synthesized using 5-benzylmercaptotetrazole (BMT) as activator, an iodine solution as oxidizing agent and a mixture of phenoxyacetic anhydride $(Pac)_2O$ in a mixture of THF/pyridine and N-methylimidazole (NMI) in THF as masking solution.

After deprotection in the conditions described above, the oligonucleotides corresponding to the RNAs, deprotected, were analyzed by RP-HPLC (Dionex DX 600) with a nucleosil 100-5 $C_{18}$ column (150×4.6 mm; Macherey-Nagel), by MALDI-TOF MS (Voyager Perspective Biosystems) and finally purified by HPLC on a Delta-Pak column (7.8×300 mm 15μ $C_{18}$ 100 Å; Waters).

The RNAs designated ON1 to ON5 were obtained and had the formulas shown in Table 2 below:

TABLE 2

| $ON^{[a]}$ SEQ ID NO | 5'-sequence-3' | $CT^{[b]}$ | $OY^{[c]}$ | $AY^{[d]}$ | Raw material$^{[e]}$ |
| --- | --- | --- | --- | --- | --- |
| 1 | $U_{12}dC$ | 180 | 96.5 | 99.7 | n.d.$^{[f]}$ |
| 2 | $U_{19}TT$ | 180 | 94.2 | 99.7 | 140 |
| 3 | CCC GUA GCU GTT | 180 | 91.1 | 99.1 | 86 |
| 4 | UGC AUC CUC GAU GGU AAC GdCT | 300 | 82.1 | 99.0 | 130 |
| 5 | CGU UAC CAU CGA GCA UCC AdAT | 300 | 83.8 | 99.1 | 125 |

$^{[a]}$ON = oligoribonucleotides
$^{[b]}$ = coupling time (s) in the automated synthesis cycle
$^{[c]}$OY = overall yield in coupling (%)
$^{[d]}$AY = average coupling yield per step
$^{[e]}$ = total raw material (O.D. Units = optical density) measured at 260 nm by UV absorption
$^{[f]}$n.d = not determined.

Example 6

Synthesis of 2'-O-acyloxymethyl-5'-O-(4,4'-dimethoxytrityl)uridine-3'-O-(2-cyanoethyl-N,N-diisopropylphosphoroamidite monomers 12a-d In this example, the ribonucleotide monomers of formula III in which the nucleic acid base is uracil, the group protecting the hydroxyl in position 5' of the ribose is a dimethoxytrityl group and the group protecting the hydroxyl in position 2' of the ribose is either an isobutyryloxymethyl group (compound 12a: 2'-O-isobutyryloxymethyl-3'-O-(2-cyanoethyl-N,N-diisopropylphosphoroamidite)-5'-O-(4,4'-dimethoxytrityl)uridine))), or a butyryloxymethyl group (compound 12b: 2'-O-butyryloxymethyl-3'-O-(2-cyanoethyl-N,N-diisopropylphosphoroamidite)-5'-O-(4,4'-dimethoxytrityl)uridine, or a propionyloxymethyl group (compound 12c: 2'-O-propionyloxymethyl-3'-O-(2-cyanoethyl-N,N-diisopropylphosphoroamidite)-5'-O-(4,4'-dimethoxytrityl) uridine))), or an acetyloxymethyl group: (compound 12d: 2'-O-acetyloxymethyl-3'-O-(2-cyanoethyl-N,N-diisopropylphosphoroamidite)-5'-O-(4,4'-dimethoxytrityl)uridine were synthesized according to the following general scheme:

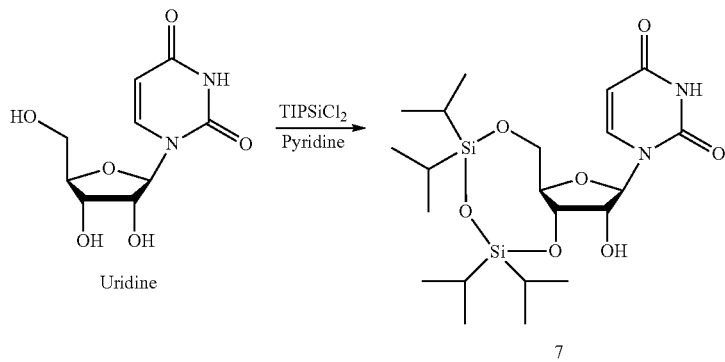
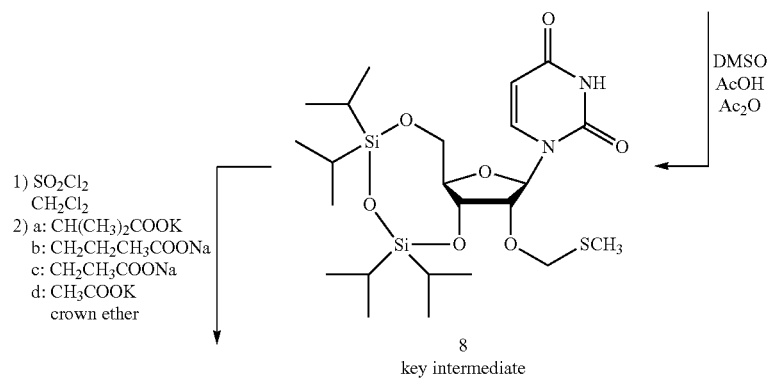
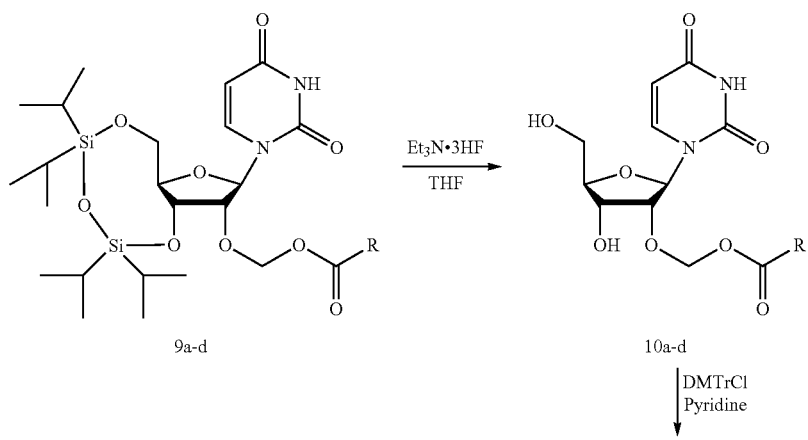
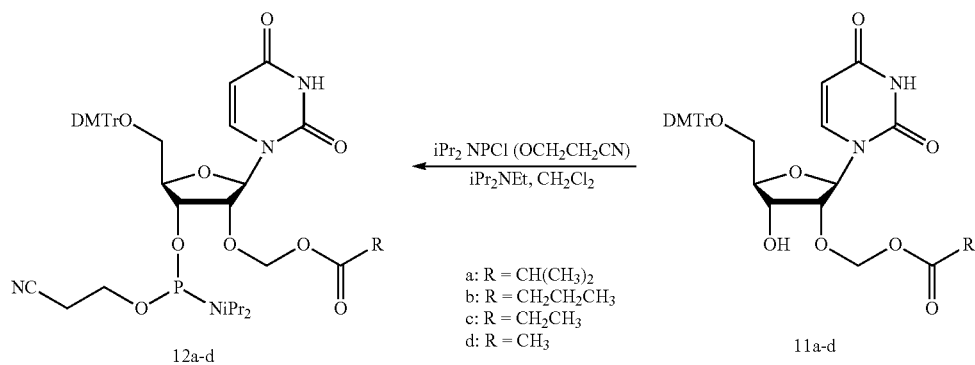

The first step of this synthesis consists of preparing the following compounds 9a to 9d respectively:

2'-O-isobutyryloxymethyl-3',5'-O-(tetraisopropyldisiloxane-1,3-diyl)uridine (9a), 2'-O-butyryloxymethyl-3',5'-O-(tetraisopropyldisiloxane-1,3-diyl)uridine (9b), 2'-O-propionyloxymethyl-3',5'-O-(tetraisopropyldisiloxane-1,3-diyl)uridine (9c), 2'-O-acetyloxymethyl-3',5'-O-(tetraisopropyldisiloxane-1,3-diyl)uridine (9d).

The procedure is as follows:

A 1.0M solution of sulfuryl chloride in $CH_2Cl_2$ (7.0 mL, 7.0 mmol, 1.25 eq) was added dropwise, under argon, to a solution of 2'-O-methylthiomethyl-3',5'-O-(tetraisopropyldisiloxane-1,3-diyl)uridine 8 (3.07 g, 5.61 mmol, 1 eq) in $CH_2Cl_2$ (25 mL). The reaction mixture was stirred at room temperature for 2 hours. After the end of the reaction, the chloromethyl ether derivative was obtained in the form of brown foam after evaporation of the solvent and was used directly in the next step.

A solution of potassium isobutyrate (1.22 g, 9.60 mmol, 1.72 eq), or of sodium butyrate (1.06 g, 9.60 mmol, 1.72 eq) or of sodium propionate (922 mg, 9.60 mmol, 1.72 eq), or of potassium acetate (926 mg, 9.60 mmol, 1.72 eq) and of dibenzo crown ether-18-6 (1.48 g, 4.17 mmol, 0.75 eq) in $CH_2Cl_2$ (10 mL) or of crown ether 15-5 (920 mg, 4.17 mmol, 0.75 eq), depending on the cation, was added dropwise to a solution of the chloromethyl ether derivative in $CH_2Cl_2$ (20 mL). After stirring at room temperature for 3 hours, the mixture was diluted with ethyl acetate and washed with water. Extraction with EtOAc was performed and the extract was dried over $Na_2SO_4$. After concentration of the solvent, the crown ether precipitate (only dibenzo crown ether 18-6) was removed by filtration and the filtrate was evaporated. The reaction mixture was submitted to silica gel chromatography with a gradient of EtOAc (0-50%) in cyclohexane. The desired compounds 9a, 9b, 9c and 9d were obtained in the form of white foams after evaporation of the solvent.

9a. (2.30 g, 70%). $^1$H NMR (400 MHz, HH—COSY, CDCl$_3$): 8.81 (s, 1H, NH); 7.80 (d, $J_{H-6/H-5}$=8.1 Hz, 1H, H-6); 5.70 (s, 1H, H-1'); 5.62 (d, $J_{H-5/H-6}$=8.1 Hz, 1H, H-5); 5.45 (2d$_{AB}$, $J_{AB}$=6.5 Hz, 2H, OCH$_2$O); 4.25-4.14 (m, 3H, H-2', H-3', H-5a'); 4.06 (dd, J=1.8 Hz, J=9.5 Hz, 1H, H-4'); 3.90 (dd, $J_{H5'b/H4'}$=2.4 Hz, J=13.6 Hz, 1H, H-5'b); 2.54 (hept, J=7.0 Hz, 1H, C(O)CH); 1.18-0.83 (m, 22H, iPr).

$^{13}$C NMR (100 MHz, CDCl$_3$): 176.6 (OC=O); 163.6 (C=O); 149.6 (C=O); 139.4 (C-6); 101.6 (C-5); 89.1 (C-1'); 87.6 (OCH$_2$O); 81.7 (C-4'); 81.3 (C-2'); 67.8 (C-3'); 59.3 (C-5'); 33.9 (C(O)CH) 18.8-18.7-17.5-17.6-17.4-17.3-17.2-17.1-16.9-16.8 (CH$_3$, iPr); 13.4-13.2-13.1-12.9-12.5 (CH, iPr).

9b. (2.90 g, 89%). $^1$H NMR (400 MHz, HH—COSY, CDCl$_3$): 8.80 (s, 1H, NH); 7.79 (d, $J_{H-6/H-5}$=8.1 Hz, 1H, H-6); 5.66 (s, 1H, H-1'); 5.61 (dd, $J_{H-5/H-6}$=8.1 Hz, $J_{H-5/NH}$=2.1 Hz, 1H, H-5); 5.46 (s, 2H, OCH$_2$O); 4.19-4.13 (m, 3H, H-2', H-3', H-5a'); 4.06 (dd, $J_{H-4'/H-5'b}$=1.8 Hz, J=9.2 Hz, 1H, H-4'); 3.90 (dd, $J_{H-5'b/H-4'}$=2.3 Hz, J=13.6 Hz, 1H, H-5'b); 2.28 (td, J=7.4 Hz, J=1.3 Hz, 2H, C(O)CH$_2$); 1.60 (sext, J=7.4 Hz, 2H, CH$_{2\beta}$); 1.03-0.92 (m, 28H, iPr); 0.89 (t, J=7.4 Hz, 3H, CH$_{3\gamma}$).

$^{13}$C NMR (100 MHz, CDCl$_3$): 173.2 (OC=O); 163.3 (C=O); 149.7 (C=O); 139.4 (C-6); 101.6 (C-5); 89.2 (C-1'); 87.5 (OCH$_2$O); 81.7 (C-4'); 81.3 (C-2'); 67.8 (C-3'); 59.3 (C-5'); 36.1 (C(O)CH$_2$); 18.1 (CH$_{2\beta}$); 17.5-17.4-17.3-17.2-17.1-17.0-16.9-13.6-13.4-13.0-12.9-12.5 (iPr, TIPS and CH$_{3\gamma}$).

9c. (2.37 g, 77%). $^1$H NMR (400 MHz, HH—COSY, CDCl$_3$): 9.18 (s, 1H, NH); 7.80 (d, $J_{H-6/H-5}$=8.2 Hz, 1H, H-6); 5.67 (s, 1H, H-1'); 5.61 (dd, $J_{H-5/H-6}$=8.1 Hz, $J_{H-5/NH}$=1.6 Hz, 1H, H-5); 5.45 (s, 2H, OCH$_2$O); 4.20-4.13 (m, 3H, H-2', H-3', H-5a'); 4.06 (dd, $J_{H-4'/H-5'b}$=1.7 Hz, J=9, Hz, 1H, H-4'); 3.90 (dd, $J_{H-5'b/H-4'}$=2.1 Hz, J=13.6 Hz, 1H, H-5'b); 2.34 (q, J=7.6 Hz, 2H, C(O)CH$_2$); 1.08 (t, J=7.5 Hz, 3H, CH$_{3\beta}$); 1.3-0.88 (m, 28H, iPr).

$^{13}$C NMR (100 MHz, CDCl$_3$): 174.0 (OC=O); 163.6 (C=O); 149.8 (C=O); 139.3 (C-6); 101.6 (C-5); 89.2 (C-1'); 87.5 (OCH$_2$O); 81.7 (C-4'); 81.3 (C-2'); 67.7 (C-3'); 59.3 (C-5'); 27.5 (C(O)C$_\alpha$); 17.5-17.4-17.3-17.2-17.1-17.0-16.8-13.4-13.0-12.9-12.5 (iPr, TIPS); 8.8 (CH$_{3\beta}$).

9d. Identification of this compound is identical to that described for the same compound in Parey et al., "*First Evaluation of Acyloxymethyl or Acylthiomethyl Groups as Biolabile 2'-O-Protections of RNA*", Organic Letters, 2006, Vol. 8, No. 17, 3869-3872.

Then the compounds 2'-o-isobutyryloxymethyl-uridine 10a, 2'-O-butyryloxymethyl-uridine 10b, 2'-O-propionyloxymethyl-uridine 10c and 2'-O-acetyloxymethyl-uridine 10d were synthesized as follows:

A solution of Et$_3$N.3HF (for 9a: 767 µL, 15.68 mmol, 4 eq; for 9b: 970 µL, 19.80 mmol, 4 eq; for 9c: 865 µL, 17.64 mmol, 4, eq and for 9d: 1017 µL, 20.76 mmol, 4 eq) was added to a solution of 9a (2.30 g, 3.92 mmol, 1 eq) or 9b (2.90 g, 4.94 mmol, 1 eq) or 9c (2.37 g, 4.41 mmol, 1 eq) or 9d (2.90 g, 5.19 mmol, 1 eq). After stirring for between 1.5 h and 5 h at room temperature, deprotection was complete and the reaction mixture was treated with triethylammonium acetate buffer (2M, pH 7), and then evaporated. The raw mixture was purified by silica gel chromatography with a gradient of MeOH (0-4.5%) in $CH_2Cl_2$. The desired compounds 10a to 10d were obtained in the form of white powders after lyophilization with dioxane.

10a. (1.25 g, 93%). $^1$H NMR (400 MHz, HH—COSY, DMSO): 11.38 (s, 1H, NH); 7.2 (d, $J_{H-6/H-5}$=8.2 Hz, 1H, H-6); 5.89 (d, $J_{H-1'/H-2'}$=5.4 Hz, 1H, H-1'); 5.68 (d, $J_{H-5/H-6}$=8.0 Hz, 1H, H-5); 5.37, 5.3 (2d$_{AB}$, $J_{AB}$=6.5 Hz 2H, OCH$_2$O); 5.32 (s, 1H, OH-3'); 5.20 (s, 1H, OH-5'); 4.26 (t, J=5.2 Hz, 1H, H-2'); 4.14 (s, 1H, H-3'); 3.88 (dd, $J_{H-4'/H-5'b}$=3.0 Hz, J=6.9 Hz, 1H, H-4'); 3.65 (dd, $J_{H-5'a/H-4'}$=2.3 Hz, $J_{H-5'a/H-5'b}$=11.9 Hz, 1H, H-5' a); 3.57 (dd, $J_{H-5'b/H-4'}$=2.5 Hz, $J_{H-5'b/H-5'a}$=11.8 Hz, 1H, H-5'b); 2.50 (hept, $J_{CH/CH3}$=7.0 Hz, 1H, C(O)CH); 1.07 (d, $J_{CH3/CH}$=7.0 Hz, 3H, CH$_3$), 1.06 (d, $J_{CH3/CH}$=7.0 Hz, 3H, CH$_3$).

$^{13}$C NMR (100 MHz, DMSO): 176.0 (OC=O); 163.5 (C=O); 151.0 (C=O); 140.9 (C-6); 102.4 (C-5); 88.0 (OCH$_2$O); 86.4 (C-1'); 85.6 (C-4'); 81.1 (C-2'); 69.1 (C-3'); 61.1 (C-5'); 33.7 (C(O)CH) 18.9 (CH$_3$, 2C).

10b. (1.56 g, 92%). $^1$H NMR (400 MHz, HH—COSY, DMSO): 11.42 (s, 1H, NH); 7.92 (d, $J_{H-6/H-5}$=8.1 Hz, 1H, H-6); 5.94 (d, $J_{H-1'/H-2'}$=5.5 Hz, 1H, H-1'); 5.73 (d, $J_{H-5/H-6}$=8.1 Hz, 1H, H-5); 5.42, 5.25 (2d$_{AB}$, $J_{AB}$=6.5 Hz 2H, OCH$_2$O); 5.35 (s, 1H, OH-3'); 5.22 (s, 1H, OH-5'); 4.30 (t, $J_{H-2'/H-3'}$=5.3 Hz, 1H, H-2'); 4.19 (dd, $J_{H-3'/H-2'}$=5.2 Hz, $J_{H-3'/H-4'}$=9.3 Hz, 1H, H-3'); 3.93 (dd, $J_{H-4'/H-5'b}$=3.1 Hz, J=6.8 Hz, 1H, H-4'); 3.70 (d, $J_{H-5'a/H-5'b}$=12.0 Hz, 1H, H-5' a); 3.62 (d, $J_{H-5'b/H-5'a}$=12.0 Hz, 1H, H-5'b); 2.30 (t, $J_{CH2\alpha/CH2\beta}$=7.3 Hz, 2H, C(O)CH$_{2\alpha}$); 1.56 (sext, $J_{CH2\beta/CH2\alpha}$=$J_{CH2\beta/CH3\gamma}$=7.4 Hz, 2H, CH$_{2\beta}$), 0.91 (t, $J_{CH3\gamma/CH2\beta}$=7.4 Hz, 3H, CH$_3$).

$^{13}$C NMR (100 MHz, DMSO): 172.2 (OC=O); 163.0 (C=O); 151.0 (C=O); 140.4 (C-6); 101.9 (C-5); 87.5 (OCH$_2$O); 86.0 (C-1'); 85.1 (C-4'); 80.7 (C-2'); 68.7 (C-3'); 60.6 (C-5'); 35.3 (C(O)CH$_{2\alpha}$); 17.6 (CH$_{2\beta}$); 13.3 (CH$_{3\gamma}$).

10c. (1.25 g, 86%). $^1$H NMR (400 MHz, HH—COSY, DMSO): 11.39 (s, 1H, NH); 7.93 (d, $J_{H-6/H-5}$=8.1 Hz, 1H, H-6); 5.89 (d, $J_{H-1'/H-2'}$=3.3 Hz, 1H, H-1'); 5.69 (d, $J_{H-5/H-6}$=8.1 Hz, 1H, H-5); 5.36, 5.23 (2d$_{AB}$, $J_{AB}$=6.5 Hz 2H, OCH$_2$O);

4.25 (t, $J_{H-2'/H-3'}$=5.2 Hz, 1H, H-2'); 4.14 (t, J=4.5 Hz, 1H, H-3'); 3.88 (dd, $J_{H-4'/H-5'b}$=3.0 Hz, J=7.0 Hz, 1H, H-4'); 3.68-3.56 (m, 2H, H-5' a; H-5' b); 2.30 (q, $J_{CH2\alpha/CH3\beta}$=7.5 Hz, 2H, C(O)CH$_{2\alpha}$); 1.01 (t, $J_{CH3\beta/CH2}$=7.5 Hz, 3H, CH$_{3\beta}$).
$^{13}$C NMR (100 MHz, DMSO): 173.0 (OC=O); 163.0 (C=O); 151.5 (C=O); 140.4 (C-6); 101.9 (C-5); 87.7 (OCH$_2$O); 86.1 (C-1'); 85.0 (C-4'); 80.8 (C-2'); 68.6 (C-3'); 60.5 (C-5'); 26.8 (C(O)CH$_{2\alpha}$); 8.6 (CH$_{3\beta}$).

10d. Identification of this compound is identical to that described for the same compound in Parey et al., "*First Evaluation of Acyloxymethyl or Acylthiomethyl Groups as Biolabile 2'-O-Protections of RNA*", Organic Letters, 2006, Vol. 8, No. 17, 3869-3872.

Next, the following compounds 11a to 11d were synthesized:
2'-O-isobutyryloxymethyl-5'-O-(4,4'-dimethoxytrityl)uridine 11a,
2'-O-butyryloxymethyl-5'-O-(4,4'-dimethoxytrityl)uridine 11b,
2'-O-propionyloxymethyl-5'-O-(4,4'-dimethoxytrityl)uridine 11c
and 2'-O-acetyloxymethyl-5'-O-(4,4'-dimethoxytrityl)uridine 11d.

For this, compounds 10a (1.25 g, 3.64 mmol, 1 eq), 10b (1.46 g, 4.25 mmol, 1, eq), 10c (1.15 g, 3.49 mmol, 1 eq) and 10d (1.51 g, 4.77 mmol, 1 eq) were dried by coevaporation three times with anhydrous pyridine. Then the solutions of 10a to 10d in anhydrous pyridine (20 mL) were treated with dimethoxytrityl chloride (1.2 eq) added in small portions in 15 minutes. The reaction mixtures were stirred for 2 to 4 hours at room temperature under argon. At the end of reaction, the mixtures were concentrated and CH$_2$Cl$_2$ was added. The solutions were poured into saturated NaHCO$_3$ solution. Extractions with CH$_2$Cl$_2$ were carried out and the extracts were dried over Na$_2$SO$_4$. The mixtures obtained after removal of the solvent were submitted to silica gel chromatography with a gradient of CH$_2$Cl$_2$ (80-100%) in cyclohexane with 1% of pyridine, then of MeOH (0-1%) in CH$_2$Cl$_2$ with 1% of pyridine. The desired compounds 11a to 11d were obtained in the form of white foams after evaporation of the solvent.

11a. (1.89 g, 79%). $^1$H NMR (400 MHz, HH—COSY, CDCl$_3$): 9.40 (s, 1H, NH); 7.93 (d, $J_{H-6/H-5}$=8.2 Hz, 1H, H-6); 7.32-7.08 (m, 10H, H$_{ar}$); 6.79-6.75 (m, 3H, H$_{ar}$); 5.88 (d, $J_{H-1'/H-2'}$=1.8 Hz, 1H, H-1'); 5.50, 5.38 (2d$_{AB}$, $J_{AB}$=6.3 Hz, 2H, OCH$_2$O); 5.23 (d, $J_{H-5/H-6}$=8.6 Hz, 1H, H-5); 4.39 (m, 1H, H-3'); 4.25 (dd, $J_{H-2'/H-1'}$=1.8 Hz, $J_{H-2'/H-3'}$=5.2 Hz, 1H, H-2'); 3.95 (td, $J_{H-4'/H-5'a}$=$J_{H-4'/H-5'b}$=2.1 Hz, $J_{H-4'/H-3'}$=7.6 Hz, 1H, H-4'); 3.72, 3.71 (2s, 6H, OCH$_3$); 3.46 (m, 2H, H-5'a, H-5' b); 2.52 (hept, $J_{CH/(CH3)2}$=7.0 Hz, 1H, C(O)CH); 1.11 (2d, $J_{CH3/CH}$=7.0 Hz, 6H, CH$_3$)
$^{13}$C NMR (100 MHz, CDCl$_3$): 176.6 (OC=O); 163.4, 150.3 (C=O); 158.8-158.7-144.3-135.2-135.0 (Cq arom.); 139.7 (C-6); 130.2-130.1-129.2-129.0-128.2-128.1-128.0-127.2-125.3-123.8-113.3-113.1 (CH arom.); 102.2 (C-5); 88.2 (C-1'); 87.7 (OCH$_2$O); 87.1 (OCq, DMTr); 83.2 (C-4'); 82.1 (C-2'); 68.5 (C-3'); 61.2 (C-5'); 55.3 (OCH$_3$, DMTr); 34.0 (C(O)CH); 17.8 (CH$_3$, iPr).

11b. (2.26 g, 79%). $^1$H NMR (400 MHz, HH—COSY, CDCl$_3$): 9.20 (s, 1H, NH); 7.91 (d, $J_{H-6/H-5}$=8.2 Hz, 1H, H-6); 7.33-7.14 (m, 10H, H$_{ar}$); 6.79-6.75 (m, 3H, H$_{ar}$); 5.88 (d, $J_{H-1'/H-2'}$=1.8 Hz, 1H, H-1'); 5.48, 5.38 (2d$_{AB}$, $J_{AB}$=6.3 Hz 2H, OCH$_2$O); 5.23 (dd, $J_{H-5/NH}$=1.9 Hz, $J_{H-5/H-6}$=8.2 Hz, 1H, H-5); 4.43-4.37 (m, 1H, H-3'); 4.26-4.24 (m, 1H, H-2'); 3.72, 3.71 (2s, 6H, OCH$_3$); 3.96-3.94 (m, 1H, H-4'); 3.50-3.42 (m, 2H, H-5'a, H-5'b); 2.47 (d, $J_{OH-3'/H-3'}$=8.9 Hz, 1H, OH-3'); 2.27 (t, J=7.5 Hz, 2H, C(O)CH$_{2\alpha}$); 1.58 (sext, $J_{CH2\beta/CH2\alpha}$=$J_{CH2\beta/CH3\gamma}$=7.5 Hz, 2H, CH$_{2\beta}$); 0.88 (t, $J_{CH3\gamma/CH2\beta}$=7.5 Hz, 3H, CH$_{3\gamma}$).
$^{13}$C NMR (100 MHz, CDCl$_3$): 173.1 (OC=O); 163.2, 150.2 (C=O); 158.8-158.7-144.3-135.2-135.0 (Cq arom.); 139.8 (C-6); 130.2-130.1-129.1-129.0-128.1-128.0-127.8-127.2-113.3-113.2-113.1 (CH arom.); 102.2 (C-5); 88.1 (C-1'); 87.7 (OCH$_2$O); 87.1 (OCq, DMTr); 83.2 (C-4'); 82.0 (C-2'); 68.6 (C-3'); 61.2 (C-5'); 55.3 (OCH$_3$, DMTr); 36.1 (C(O)CH$_2$); 18.1 (CH$_{2\beta}$); 13.6 (CH$_{3\gamma}$).

11c. (1.81 g, 82%). $^1$H NMR (400 MHz, HH—COSY, CDCl$_3$): 9.27 (s, 1H, NH); 7.91 (d, $J_{H-6/H-5}$=8.1 Hz, 1H, H-6); 7.31-7.08 (m, 10H, H$_{ar}$); 6.78-6.74 (m, 3H, H$_{ar}$); 5.88 (d, $J_{H-1'/H-2'}$=1.7 Hz, 1H, H-1'); 5.47, 5.39 (2d$_{AB}$, $J_{AB}$=6.4 Hz 2H, OCH$_2$O); 5.22 (dd, $J_{H-5/NH}$=1.0 Hz, $J_{H-5/H-6}$=8.1 Hz, 1H, H-5); 4.43-4.37 (m, 1H, H-3'); 4.25 (m, 1H, H-2'); 3.95 (d, J=7.5 Hz, 1H, H-4'); 3.72, 3.71 (2s, 6H, OCH$_3$); 3.47-3.42 (m, 2H, H-5'a, H-5'b); 2.48 (d, $J_{OH-3'/H-3'}$=8.5 Hz, 1H, OH-3'); 2.31 (q, J=7.5 Hz, 2H, C(O)CH$_{2\alpha}$); 1.07 (t, $J_{CH3\beta/CH2\alpha}$=7.5 Hz, 3H, CH$_{3\beta}$).
$^{13}$C NMR (100 MHz, CDCl$_3$): 174.0 (OC=O); 163.4, 150.2 (C=O); 158.7-144.3-141.5-135.3-135.0 (Cq arom.); 139.9 (C-6); 130.2-130.1-129.1-128.1-128.0-127.8-127.7-127.2-127.1-113.3-113.2 (CH arom.); 102.2 (C-5); 88.1 (C-1'); 87.8 (OCH$_2$O); 87.1 (OCq, DMTr); 83.2 (C-4'); 82.0 (C-2'); 68.6 (C-3'); 61.2 (C-5'); 55.3 (2C, OCH$_3$, DMTr); 27.5 (C(O)CH$_2$); 8.8 (CH$_{3\beta}$).

11d. Identification of this compound is identical to that described for the same compound in Parey et al., "*First Evaluation of Acyloxymethyl or Acylthiomethyl Groups as Biolabile 2'-O-Protections of RNA*", Organic Letters, 2006, Vol. 8, No. 17, 3869-3872.

Finally, the monomers of formula III were synthesized.

2'-O-isobutyryloxymethyl-3'-O-(2-cyanoethyl N,N-diisopropylphosphoroamidite)-5-O-(4,4'-dimethoxytrityl)uridine 12a, 2'-O-butyryloxymethyl-3'-O-(2-cyanoethyl-N,N-diisopropylphosphoroamidite)-5'-O-(4,4'-dimethoxytrityl)uridine 12b, 2'-O-propionyloxymethyl-3'-O-(2-cyanoethyl-N,N-diisopropylphosphoroamidite)-5'-O-(4,4'-dimethoxytrityl)uridine 12c and 2'-O-acetyloxymethyl-3'-O-(2-cyanoethyl-N,N-diisopropylphosphoroamidite)-5'-O-(4, 4'-dimethoxytrityl)uridine 12d.

For this, compounds 11a (1.77 g, 2.74 mmol, 1 eq), 11b (2.17 g, 3.36 mmol, 11c (1.80 g, 2.85 mmol) and 11d (1.65 g, 2, 67 mmol) were dried by coevaporation three times with anhydrous CH$_3$CN. Then the residue was dissolved in anhydrous CH$_2$Cl$_2$ (14 mL) and a mixture of N,N-diisopropylethylamine (for 11a: 859 μL, 4.93 mmol, 1.8 eq; for 11b: 1050 μL, 6.06 mmol, 1.8 eq; for 11c: 894 μL, 5.13 mmol, 1.8 eq; and for 11d: 838 μL, 4.81 mmol, 1.8 eq), and 2-cyanoethyl-N,N-diisopropylchlorophosphoroamidite (for 11a: 917 μL, 4.11 mmol, 1.5 eq; for 11b: 1120 μL, 5.04 mmol, 1.5 eq; for 11c: 954 μL, 4.28 mmol, 1.5 eq; for 11d: 895 μL, 4.01 mmol, 1.5 eq) and CH$_2$Cl$_2$ (2 mL) was added dropwise. The mixture was stirred under argon, at room temperature, for 3 hours. After the end of reaction, ethyl acetate was added, the reaction mixture was poured into saturated NaHCO$_3$ solution and extractions with EtOAc were applied. The mixture obtained after drying the extract over Na$_2$SO$_4$ and removal of the solvent was purified by silica gel chromatography with a gradient of CH$_2$Cl$_2$ (50-100%) in cyclohexane with 1% of pyridine. The desired phosphoroamidites 12a to 12d were obtained in the form of white foams after evaporation of the solvent.

12a. (1.63 g, 70%). $^{31}$P NMR (121 MHz, CD$_3$CN): δ (ppm): 150.35, 149.15.

12b. (1.85 g, 66%). $^{31}$P NMR (121 MHz, CD$_3$CN): δ (ppm): 150.31, 149.09.

12c. (1.93 g, 81%). $^{31}$P NMR (121 MHz, CD$_3$CN): δ (ppm): 150.30, 149.01.

12d. (1.14 g, 52%). $^{31}$P NMR (121 MHz, CD$_3$CN): δ (ppm): 150.31, 148.96.

Example 7

Synthesis of Single-Stranded RNA of Formula I by Phosphoroamidite Chemistry with X$_3$ which is an Isobutyryloxymethyl Group or a Butyryloxymethyl Group or a Propionyloxymethyl Group or an Acetyloxymethyl Group Single-stranded RNAs were synthesized starting from the monomers 12a-d obtained in example 6.

These protected RNAs of formula I were prepared according to a method identical to that described in example 5 for obtaining ON4 to ON5.

The RNAs designated ON6 to ON9 of identical sequence U$_{19}$TT were obtained with the results shown in Table 3 below:

TABLE 3

| ON[a] U$_{19}$TT | X$_3$ | CT[b] | OY[c] | AY[d] | Raw material[e] |
|---|---|---|---|---|---|
| 6 | isobutyryloxymethyl | 180 | 75.9 | 98.5 | 122 |
| 7 | Butyryloxymethyl | 180 | 68.4 | 98.1 | 130 |
| 8 | Propionyloxymethyl | 180 | 77.9 | 98.7 | 100 |
| 9 | Acetyloxymethyl | 180 | 70.7 | 98.3 | 120 |

[a]ON = oligoribonucleotides
[b]= coupling time (s) in automated synthesis cycle
[c]OY = overall yield in coupling (%)
[d]AY = average coupling yield per step
[e]= total raw material (O.D. Units = optical density) measured at 260 nm by UV absorption It should be pointed out that groups X$_3$ isobutyryloxymethyl and butyryloxymethyl were removed from the RNA of formula I in 15 min by treatment with concentrated ammonia and groups X$_3$ propionyloxymethyl and acetyloxymethyl were removed in less than 5 min by treatment with concentrated ammonia even if this treatment was prolonged to 1.5 h for completely breaking the succinyl linker with the solid substrate and releasing the RNAs.

Example 8

Enzymatic Digestion of RNA

The RNAs ON4 and ON5 obtained in example 5 (2 units of OD at 260 nm) were incubated with a nuclease P1 (0.25 units) (specific for cleavage of 3'-5' internucleoside linkers) at 37° C. for 48 h.

Then an alkaline phosphatase (2.5 units) and a buffer (50 mM Tris-HCl, pH 9.3, containing 1 mM of MgCl$_2$, 0.1 mM of ZnCl$_2$ and 1 mM of spermidine; final concentrations) were added to give a total volume of 115 µl and the mixture was incubated at 37° C. for a further 24 h. The reaction mixture was analyzed by HPLC.

The RNAs were completely degraded to give the four natural ribonucleosides, proving the integrity of the 3'-5' internucleotide linkers. No nonnatural linker 2'-5' was detected.

Example 9

Test In Vitro of an siRNA Obtained by the Method of the Invention

The activity of the siRNA duplex obtained from the single-stranded RNAs ON4 and ON5 hybridized together was evaluated in an RNA interference test which targets the messenger RNA of the oncogene Ret/PTC1 implicated in papillary thyroid cancer.

This activity of the siRNA ON4/ON5 duplex obtained by the method of the invention was compared with the activity of the same siRNA AS duplex supplied by Eurogentec and synthesized by another synthesis route (2'-TBDMS method).

The cells used for testing the siRNA obtained were murine fibroblasts NIH/3T3 stably transfected with a vector pBAB expressing the human oncogene Ret/PTC1. Cell culture was performed in DMEM medium (GIBCO) containing 10% of heat-inactivated newborn calf serum (10%, GIBCO), penicillin (100 U/ml), streptomycin (100 µg/ml, GIBCO), and puromycin (2.5 µg/ml Sigma) at 37° C. with 5% CO$_2$ in a humid atmosphere.

This cell culture was then treated with the siRNA obtained from the single-stranded RNAs ON4 and ON5 as well as with the commercial siRNA AS.

One day before the treatment, $3.10^5$ cells were seeded on six-well plates. Transfection was carried out by mixing 0.05 nmol of siRNA in 50 µl of Hepes buffer 10 mM, pH 7.2, 100 mM of NaCl with 2 µg of cytofectin (GTS) in 50 µl of the same buffer. After 10 minutes of incubation at room temperature, the complexes were added to the cells in 900 µl of fresh culture medium containing serum for 24 h. The experiment was carried out in triplicate. The control sequences of the siRNA are SEQ ID NO: δ: 5'-GCCAGUGUCACCGU-CAAGGdAdG-3' and SEQ ID NO: 7: 5'-CCUUGACG-GUGACACUGGCdTdT-3' and were supplied by Eurogentec. These are nonspecific random sequences of the required mRNA.

Then detection of expression of the mRNA Ret/PTC1 was carried out by RT-PCR. The mRNA was extracted with the reagent TRIzol (Invitrogen) as indicated by the manufacturer. After determining the concentration by UV spectrometry, 1 µg of the total RNA either from the control cells, or from the treated cells was incubated with Mo-MuLV RT (Promega), as indicated by the manufacturer, in 20 µl of final volume for 1 h at 42° C. Then expression of the mRNA Ret/PTC1 was determined by PCR on 2 µl of reverse transcription products in 50 µl of reaction mixture comprising Taq Polymerase (Ozyme).

The following primers were used for amplification of Ret/PTC1 (290 pb) antisense primer: SEQ ID NO: 8: 5'-CTGCT-TCAGGACGTTGAA-3' and sense primer SEQ ID NO: 9: 5'-AGATAGAGCTGGAGACCTAC-3'.

GAPDH (531 pb), a gene coding for the enzyme glyceraldehyde 3-phosphate dehydrogenase, was used as control of functioning of the reverse transcription (RT) with the primer sequences SEQ ID NO:10: 5'-GACAACTCACTCAAGAT-TGTCAG-3' and SEQ ID NO:11: 5'-CATTGTCATACCAG-GAAATG-3'.

The PCR products were obtained after 21 or 32 cycles, respectively, and analyzed by electrophoresis on 2% agarose gel with a Tris Acetate EDTA buffer (TAE) [0.5×]. The DNA fragments were detected under UV illumination after staining with ethidium bromide and then quantification was carried out with a computer analysis system coupled to a camera (Syngene). The experiments were performed in triplicate.

These various experiments (performed in triplicate) showed that the double-stranded siRNA obtained from RNAs ON4 and ON5, themselves obtained by the method of the invention, had a better gene silencing activity (60% inhibition) than the purchased double-stranded siRNA AS of the same sequence, manufactured by the chemical method of protection with TBDMS (40% inhibition). This better activity could be explained by higher purity of the double-stranded RNA of the invention purified by RP-HPLC compared with the siRNA AS purified by PAGE.

In all cases, this result confirms the integrity and purity of the RNAs synthesized by the method of the invention.

It will be apparent to a person skilled in the art that any other groups protecting the nucleic acid bases, and the hydroxyls in position 3' and 5' of the ribose that are well known, can be used, provided that the group protecting the hydroxyl in position 3' is base-labile of the acyloxyalkyl or acylthioalkyl type.

Moreover, it will be apparent to a person skilled in the art that the treatment with ammonia used for deprotecting the hydroxyl in position 2' and the exocyclic amine functions of the nucleic acid bases of the synthesized RNA also makes it possible, at the same time, to liberate the RNA from its solid substrate, when it is bound to the solid substrate by a base-labile linker such as a succinyl linker or Q-linker.

Moreover, although in the foregoing description and the appended claims, the protecting group $X_1$ has been described as being selected from acid-labile groups, it will be apparent to a person skilled in the art that suitable fluorine-labile or base-labile groups known by a person skilled in the art can also be used for protecting the hydroxyl in position 5' of the ribose.

The invention claimed is:

1. A method of synthesis of a single-stranded RNA, characterized in that it comprises the following steps:

a) binding, to a solid substrate, of a monomer of the following formula II

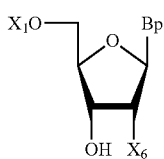

Formula II in which:
  $X_1$ is a dimethoxytrityl group,
  $X_6$ is H or a group OAc or $OX_3$ in which $X_3$ is a group of the following formula A:

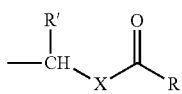

Formula A in which X is O or S, R' is H or $CH_3$, and R is selected from a linear or branched $C_1$ to $C_4$ alkyl group and a group $R_1$—O—$R_2$ in which $R_1$ is a $C_1$ to $C_2$ alkyl group and $R_2$ is a $CH_3$ or $CH_2CH_2$—O—$CH_3$ or aryl group, Bp is a natural or modified thymine nucleic acid base when $X_6$ is H or a natural or modified uracil nucleic acid base when $X_6$ is OAc or $OX_3$ or a protected natural or modified adenine nucleic acid base or a protected natural or modified cytosine nucleic acid base or a protected natural or modified guanine nucleic acid base regardless of $X_6$, b) assembly, with the monomer of formula II bound to its substrate obtained in step a), of at least one monomer of the following formula III:

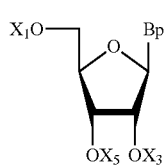

Formula III in which $X_1$, Bp, $X_3$ are as defined for formula II and $X_5$ is a 2-cyanoethyl-N,N-diisopropylphosphoroamidite group, by which a protected single-stranded RNA bound to a substrate of following formula I is obtained Formula I

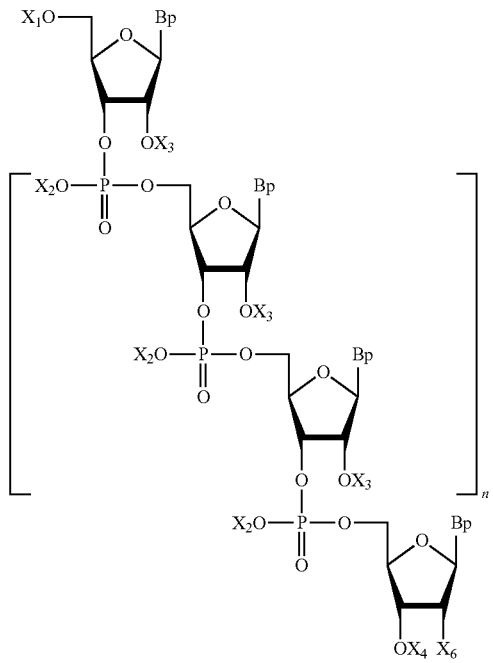

in which:
X$_1$ is H or a hydroxyl-protecting group selected from a dimethoxytrityl group, a monomethoxytrityl group and a pixyl group, preferably a dimethoxytrityl group,
X$_2$ is H or a group protecting the β-removable phosphate, preferably a cyanoethyl group,
X$_3$ is a base-labile group protecting the hydroxyls in position 2' of the ribose of the following formula A:

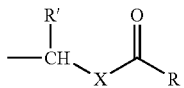

Formula A in which X is O or S, R' is H or CH$_3$, and R is selected from a linear or branched C$_1$ to C$_4$ alkyl group and a group R$_1$—O—R$_2$ in which R$_1$ is a C$_1$ to C$_2$ alkyl group and R$_2$ is a CH$_3$ or CH$_2$CH$_2$—O—CH$_3$ or aryl group, X$_4$ represents the linker-substrate assembly,
X$_6$ is H or a group OX$_3$ or OAc,
Bp is a natural or modified thymine nucleic acid base when X$_6$ is H or natural or modified uracil when X$_6$ is OX$_3$ or OAc, or protected natural or modified adenine, or protected natural or modified cytosine, or protected natural or modified guanine regardless of X$_6$, and
n is an integer greater than or equal to 0,
c) release of the protected single-stranded RNA bound to a substrate obtained in step b), by a method of released comprising a step a1) of treatment of the protected single-stranded RNA bound to a substrate of formula I with a base selected from piperidine, 1,8-diazabicyclo5.4.0 undec-7-ene (DBU), triethylamine at room temperature, to release the phosphate of the 3'-5' internucleoside linkers, when X$_2$ is different from H, followed by a step b1) of treatment of the partially released RNA obtained in step a1), with a base selected from concentrated ammonia, methylamine, potassium carbonate, at room temperature.

2. The method of synthesis of a single-stranded RNA as claimed in claim 1, characterized in that it further comprises, before step b), a step a') of synthesis of a monomer of formula III comprising the following steps:
   a) protection of the exocyclic amines of the nucleic acid bases Bp, when the nucleic acid base Bp is different from natural or modified uracil,
   b) protection of the hydroxyl in position 5' of the ribose sugar,
   c) protection of the hydroxyl in position 2' of the ribose sugar with a group of formula A, and
   d) functionalization of the hydroxyl in position 3' of the ribose sugar with a 2-cyanoethyl-N,N-diisopropylphosphoroamidite group.

3. A method of synthesis of a double-stranded RNA, characterized in that it comprises the synthesis of a single-stranded RNA according to the method as claimed in claim 1 and hybridization of the single-stranded RNA thus synthesized to a single-stranded RNA having a complementary sequence.

4. The method of synthesis as claimed in claim 2, characterized in that the double-stranded RNA is an siRNA.

5. The method of synthesis as claimed in claim 1, further comprising, after step b) and before step c), a step b') of treatment of the assembly obtained in step b) with an acidic medium and wherein step c) is a step of releasing of the protected single-stranded RNA bound to a substrate obtained in step b').

* * * * *

```
                        SEQUENCE LISTING

<160> NUMBER OF SEQ ID NOS: 11

<210> SEQ ID NO 1
<211> LENGTH: 13
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (13)..(13)
<223> OTHER INFORMATION: n is dC (deoxycytosine)
<220> FEATURE:
<223> OTHER INFORMATION: Combined DNA/RNA Sequence

<400> SEQUENCE: 1
uuuuuuuuuu uun                                                          13

<210> SEQ ID NO 2
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(21)
<223> OTHER INFORMATION: n is T (thymine)
<220> FEATURE:
<223> OTHER INFORMATION: Combined DNA/RNA Sequence

<400> SEQUENCE: 2 uuuuuuuuu uuuuuuuuun n                                                  21

<210> SEQ ID NO 3
<211> LENGTH: 12
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (11)..(12)
<223> OTHER INFORMATION: n is T (thymine)
<220> FEATURE:
<223> OTHER INFORMATION: Combined DNA/RNA Sequence

<400> SEQUENCE: 3
cccguagcug nn                                                           12

<210> SEQ ID NO 4
<211> LENGTH: 21
<212> TYPE: DNA
<213> ORGANISM: Artificial Sequence
<220> FEATURE:
```

```
<223> OTHER INFORMATION: Synthesized
<220> FEATURE:
<221> NAME/KEY: misc_feature
<222> LOCATION: (20)..(20)
<223> OTHER INFORMATION: n is dC (deoxycytosine)
<220> FEATURE:
<221> NAME/KEY: misc_feature
<222> LOCATION: (21)..(21)
<223> OTHER INFORMATION: n is T (thymine)
<220> FEATURE:
<223> OTHER INFORMATION: Combined DNA/RNA Sequence

<400> SEQUENCE: 4
ugcauccucg augguaacgn n                                                 21

<210> SEQ ID NO 5
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(20)
<223> OTHER INFORMATION: n is dA (deoxyadenosine)
<220> FEATURE:
<221> NAME/KEY: misc_feature
<222> LOCATION: (21)..(21)
<223> OTHER INFORMATION: n is T (thymine)
<220> FEATURE:
<223> OTHER INFORMATION: Combined DNA/RNA Sequence

<400> SEQUENCE: 5
cguuaccauc gagcauccan n                                                 21

<210> SEQ ID NO 6
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(20)
<223> OTHER INFORMATION: n is dA (deoxyadenine)
<220> FEATURE:
<221> NAME/KEY: misc_feature
<222> LOCATION: (21)..(21)
<223> OTHER INFORMATION: n is dG (deoxyguanine)
<220> FEATURE:
<223> OTHER INFORMATION: Combined DNA/RNA Sequence

<400> SEQUENCE: 6
gccaguguca ccgucaaggn n                                                 21

<210> SEQ ID NO 7
<211> LENGTH: 21
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(21)
<223> OTHER INFORMATION: n is dT (deoxythymine)
<220> FEATURE:
<223> OTHER INFORMATION: Combined DNA/RNA Sequence

<400> SEQUENCE: 7
ccuugacggu gacacuggcn n                                                 21

<210> SEQ ID NO 8
```

```
<211> LENGTH: 18
<212> TYPE: DNA
<213> ORGANISM: Artificial Sequence
<220> FEATURE:
<223> OTHER INFORMATION: Primer sequence

<400> SEQUENCE: 8
ctgcttcagg acgttgaa                                                 18

<210> SEQ ID NO 9
<211> LENGTH: 20
<212> TYPE: DNA
<213> ORGANISM: Artificial Sequence
<220> FEATURE:
<223> OTHER INFORMATION: Primer sequence

<400> SEQUENCE: 9
agatagagct ggagacctac                                               20

<210> SEQ ID NO 10
<211> LENGTH: 23
<212> TYPE: DNA
<213> ORGANISM: Artificial Sequence
<220> FEATURE:
<223> OTHER INFORMATION: Primer sequence

<400> SEQUENCE: 10
gacaactcac tcaagattgt cag                                           23

<210> SEQ ID NO 11
<211> LENGTH: 20
<212> TYPE: DNA
<213> ORGANISM: Artificial Sequence
<220> FEATURE:
<223> OTHER INFORMATION: Primer sequence

<400> SEQUENCE: 11
cattgtcata ccaggaaatg                                               20
```